United States Patent [19]
Gardner, Jr. et al.

[11] Patent Number: 5,420,381
[45] Date of Patent: May 30, 1995

[54] ACOUSTICAL EARMUFF

[75] Inventors: Ross Gardner, Jr., Indianapolis; Gregory L. Simon, Zionsville, both of Ind.

[73] Assignee: Cabot Safety Corporation, Southbridge, Mass.

[21] Appl. No.: 48,722

[22] Filed: Apr. 19, 1993

[51] Int. Cl.⁶ .............................................. H04R 25/00
[52] U.S. Cl. .................................................... 181/129
[58] Field of Search ..................... 181/129, 137, 135; 2/209; 381/158, 183, 187

[56] References Cited

U.S. PATENT DOCUMENTS

| | | | |
|---|---|---|---|
| 2,801,423 | 8/1957 | Shaw et al. | 2/209 |
| 4,260,575 | 4/1981 | Thew et al. | 264/154 |
| 4,465,159 | 8/1984 | Stallings | 181/129 |
| 4,471,496 | 9/1984 | Gardner, Jr. et al. | 2/209 |
| 4,682,374 | 7/1987 | Geiser | 2/209 |
| 4,958,697 | 9/1990 | Moody | 181/129 |
| 5,148,887 | 9/1992 | Murphy | 181/129 |

Primary Examiner—M. L. Gellner
Assistant Examiner—Khanh Dang

[57] ABSTRACT

An earmuff cushion providing improved attenuation is described. The cushion is a foam material having a low static stiffness, and a high dynamic stiffness, which produces improved attenuation in the earmuff in which it is used. Earmuffs made from the cushion and improved methods of making the cushion and the earmuffs are also described.

17 Claims, 17 Drawing Sheets

ACOUSTICAL EARMUFF

TECHNICAL FIELD

The field of art to which this invention pertains is hearing protection, and specifically acoustical earmuffs.

BACKGROUND ART

The use of earplugs and earmuffs are the two most useful ways to protect against hearing loss in those environments where noise levels are not able to be controlled within safe limits. In those areas where the use of earplugs is either impossible or impractical, the use of earmuffs provides a means of reducing sound intensity, in most instances to a degree even greater than that provided by the use of earplugs. Other uses for noise excluding hearing protectors include producing quiet for study, sleep, or audio purposes.

Earmuffs have advantages for intermittent use where continuous insertion and removal of earplugs would be annoying or impractical. Also, earmuffs tend to deliver higher in-field noise protection in many high frequency noise environments than most earplugs. Additional preference for earmuffs include use outdoors in cool weather and use in dry climates.

Generally, earmuffs have poorer low frequency attenuation values than earplugs. Part of the problem is because at lower frequencies of 125 to 1000 Hz the earmuff vibrates upon the earmuff cushion and flesh in a pumping mode. Most cushions are selected of a soft combination of materials to achieve conformation to the head about the ear and claim comfort because of this ease of conformation.

Most earmuffs are made up of a band section, a cup section, and a cushion section. The band section extends between the pair of muffs, and holds the muffs snugly against the head of the wearer. The cup section is typically filled with foam material, and in this combination of cup and foam is where the sound attenuation takes place. The cushion section extends around the edge of the cup, and this cushion serves two purposes, to provide comfort to the wearer, and to form a seal to assist in keeping unwanted noise away from the wearer's ears.

There is a constant search for ways to improve the comfort, sound attenuation characteristics, appearance and designs of these earmuffs (note, for example, U.S. Pat. Nos. 2,801,423; 4,260,575; 4,465,159; 4,471,496; and 4,682,374). In one of these patents, Shaw et al. U.S. Pat. No. 2,801,423, the cushion comprises a covering of pliable or flexible but non-elastic material which forms a chamber around the periphery of the rigid cup. This chamber is substantially gas evacuated and partially filled with a liquid.

Shaw et al. later redefines the preferred wall material as being polyvinyl chloride having a wall thickness of about 0.005 to about 0.01 inch and/or a dynamic Young's modules of about $5 \times 10^3$ p.s.i. FIG. 1 shows the typical attenuation achieved by an adaptation of this patent. The figure shows ANSI S3.19 Real ear attenuation vs. Calculated Attenuation (C) for Safety Supply Model 258 Ear Muffs (Liquid Cushions as Per U.S. Pat. No. 2,801,423).

The broken line on the graph indicates the calculated values and the solid line the real ear values. Depths of 0 are formulated by the following formula:

$$F_o = A_2/VM \times 35460 \quad A = 72.84 \text{ cm}^2$$
$$V = 189.90 \text{ cm}^3$$
$$M = 116.08 \text{ Gm}$$
$$F_o = 92 \text{ Hz}$$

The present invention is directed to not only products, but materials and methods for producing such earmuffs which addresses the above concerns.

BRIEF SUMMARY OF THE INVENTION

The present invention is directed to an earmuff cushion which provides improved attenuation and ease of manufacture. The cushion is made up a foam material which has a low static stiffness, and a high dynamic stiffness. This invention simplifies construction which contributes to its ease of manufacture, retains ease of conformation about the ear and this same material acts dynamically very stiff reducing the motions of the earmuff cup. Another aspect of the invention is an acoustical earmuff device containing such a cushion.

Another aspect of the invention is a method of making such a cushion, through molding the cushion by passing the ingredients through a mix/meter machine into a mold, followed by crushing the molded cushion to provide increased deflection characteristics while maintaining dynamic stiffness.

Dynamically stiff cushions made by the above process when placed on low to medium volume earmuffs, the preferred types, lead to dramatically improved attenuation results. These results exceed those predicted by equations normally employed for calculation purposes.

These, and other aspects of the invention will become apparent from the following detailed description.

DETAILED DESCRIPTION OF THE INVENTION

Figure 1:
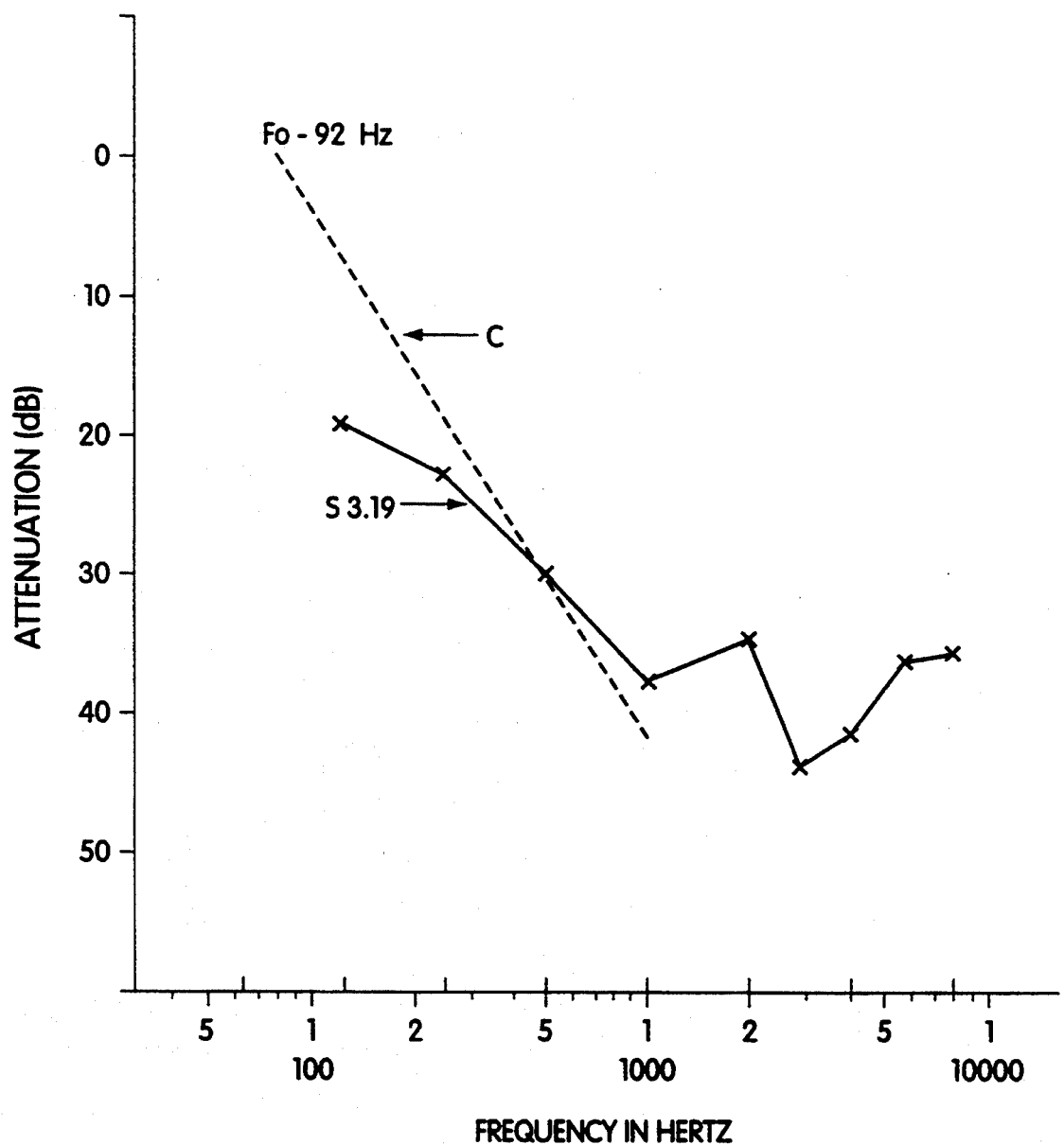
FIG. 1 shows typical attenuation of systems of the prior art.

The critical component of the cushion which provides the improved attenuation in the earmuff is its stiffness characteristics. The degree of stiffness desired is dependent upon the ability of the cushion to form an acoustical seal against the head. It has been found that material with a low static stiffness, and high dynamic stiffness, provide improved attenuation according to the present invention. These stiffness characteristics are defined in terms of dynamic complex spring constant ($K^*$), static spring constant ($K_s$), and dynamic material loss factor ($\eta$).

In order to provide the improved attenuation according to the present invention it is important that the foam cushions have a dynamic spring constant of at least 300 pounds/inch and a dynamic material loss factor of at least 0.25, and preferably a dynamic spring constant of at least 1,000 pounds/inch. It is also important that the material have a static spring constant of up to about 60 pounds/inch, and preferably up to about 30 pounds/inch. While the cushions according to the present invention can be made of any polymeric material having the above described stiffness characteristics, polyurethane material has been found to be particularly suitable, for example, because of its stability in the presence of skin oils. And while any moldable polyurethane can be used, an especially preferred material is that described in U.S. Pat. No. 3,377,296, the disclosure of which is incorporated by reference.

Polyurethane Formulations

The preferred polyurethane is diisocyanate based, preferably reacted with polyols with a portion being at least tri-functional, and having an isocyanate index of less than about 0.9.

According to Immergut and Mark (*Plasticization and Plasticizer Processes*, American Chemical Society Publications);

"Plasticization, in general refers to a change in the thermal and mechanical properties of a given polymer which involves: (a) lowering of rigidity at room temperature; (b) lowering of temperature, at which substantial deformation can be effected with not too large forces; (c) increase of elongation to break at room temperature; (d) increase of the toughness (impact strength) down to the lowest temperature of serviceability. These effects can be achieved: (1) by compounding the given polymer with low molecular weight compound or with another polymer: and (2) by introducing into the original polymer a comonomer which reduces crystallizability and increases chain flexibility."

Plasticizers have been broken into two types, internal plasticizers and external plasticizers. Internal plasticizers are actually a part of the polymer molecule—e.g., a second monomer is copolymerized into the polymer structure thereby making it less ordered, and therefore, more difficult for the chains to fit closely together. This soften the polymer—i.e., lowers the glass transition temperature (Tg) or the modulus. Usually, the internal plasticizer is a monomer whose polymer has good low temperature properties.

External plasticizers are compounds mixed in with the polymer which makes it more difficult for the chains to fit closely together. This softens the polymer—e.g., lowers Tg or the modulus. External plasticizers are often categorized as primary or secondary defining degree of compatibility or in terms of it efficiency or permanence.

Polyurethanes are typically block co-polymers consisting of polyester polyols and/or polyether polyols reacted with isocyanates having a functionality of 2 or more. Sometimes the term polymers of isocyanates is used to better define systems where water or amine terminated compounds are reacted resulting in polyureas. Here polyurethane will be used all inclusively.

When using a polymer polyol as a reactant, it is a plasticizer. Generally, the larger the polymer chain lengths for a particular type polyol the lower Tg. Types of polyols could also be referred to as having different efficiencies. (Polyethers being more efficient than polyesters.) Likewise, polyols could be considered more efficient than polyamines.

Monofunctional reactants produce side chains which act as plasticizers. However, they may be more or less efficient than the plasticizer they replace. External plasticizer may be employed in polyurethane. Compatibility is quite important here and often a preferred approach has been to under index the system. The best way of ensuring compatibility is to use segments of the polymer itself as plasticizer.

Underindexing is the in situ production of external plasticizer at the same time producing more dangling polymer segments. Underindexing is not new to the art and was used in the early 1960's to produce soft foams for use in mattresses and the like. See U.S. Pat. No. 3,377,296 and *Cellular Plastics—Today's Technology*, Apr. 24–25, 1963, "Technology of Super Soft Flexible Urethane Foams" by Dwyer, Kaplan, Pirer and Stone.

The cushions according to the present invention use di- and tri- functional polyether polyols of varying molecular weight, underindexing and density adjustments as methods of formulating compositions which produce molded, dynamically stiff, noise excluding earmuff cushions. At least a portion of the polyol used should have trifunctionality (so as to produce a solid foam as opposed to simply a liquid polyurethane). Surfactant combinations are employed to maintain closed cells, a requirement for noise excluding earmuff cushions. Lowering of the isocyanate index (NCO/OH) softens as does increasing polyol chain segment length.

The cushions of the present invention will provide improvement in attenuation both in use with the standard types of earmuffs generally on the market, but without the bladders currently used.

Figure 2:
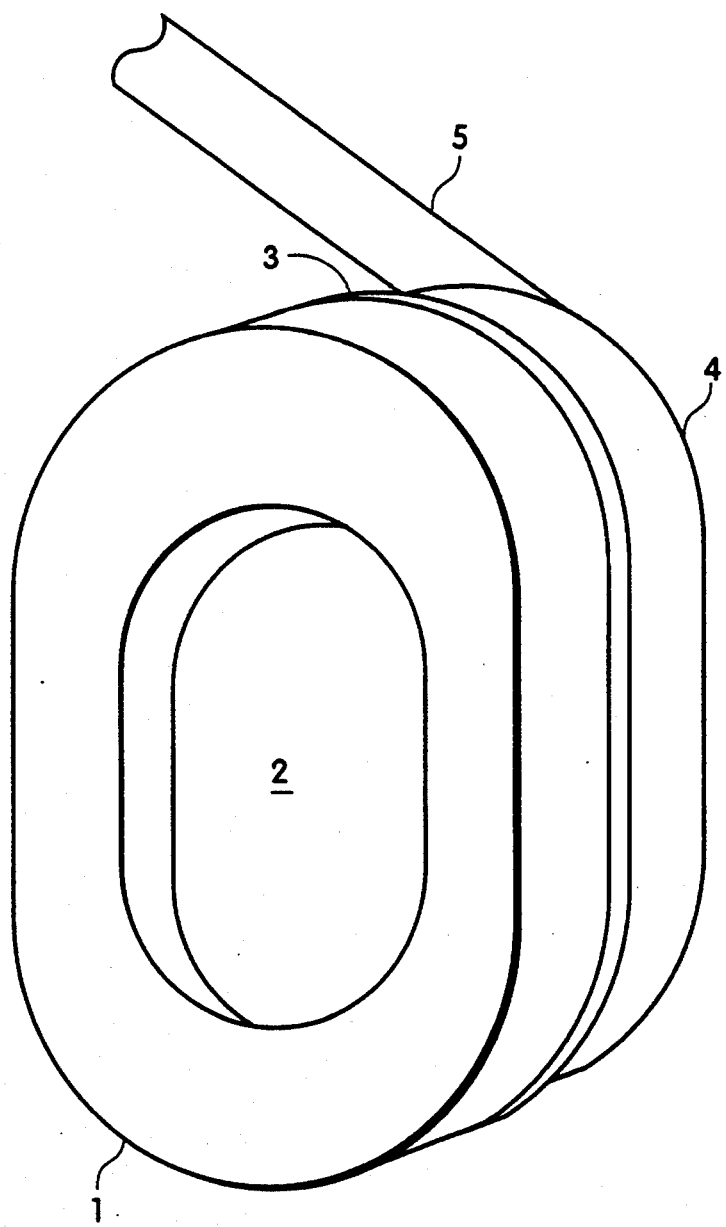
FIG. 2 shows a standard earmuff containing a cushion according to the present invention.

In FIG. 2, the cushion 1, is attached to the seal plate 3, typically by a conventional pressure adhesive such as an acrylic material (not shown). The seal plate is similarly attached to the cup 4, again by conventional methods such as ultrasonic welding. The headband 5 is attached to the cup, by typical mechanical means such as through a grommet (not shown), e.g. like those used in the conventional E-A-R ® 1000-3000 Model muffs. The foam liners 2 lining the inner surfaces of the cup 4, can be made of conventional open cell foam materials, such as conventional polyurethanes as are currently used. Elimination of the cushion bladder provides the advantages of material savings and labor savings, in addition to the increased attenuation. Although the foam according to the present invention can be used inside a conventional bladder system and some of the attenuation advantages of the present system realized, the manufacturing advantages would not be realized.

Figure 3:
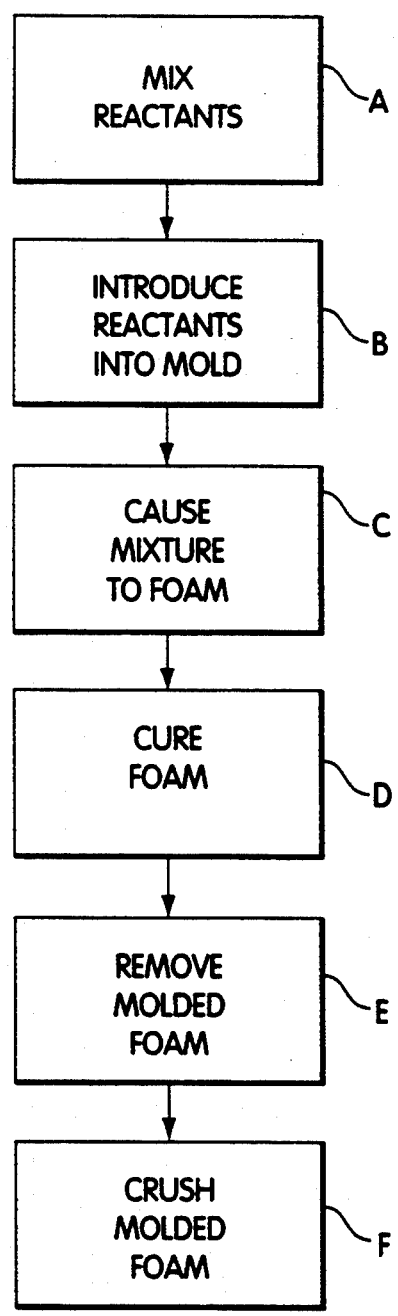
FIG. 3 shows a flow chart of a molding process for making cushions according to the present invention.

The method for making the cushions according to the present invention can be described by reference to FIG. 3. The reactants described in Table 1 are mixed in conventional mixing equipment. This foam reaction mixture can be premixed and introduced into the mold or mixed as separate reactant streams and injected as a single stream right into the preheated mold, for example in a conventional mix/meter molding apparatus, and is next introduced into the preheated mold, causing foaming to take place. The injection can take place at low or high pressures ranging from, for example, 50 to 300 pounds per square inch. The temperature is allowed to remain sufficiently high to cure the foam in the shape of the cushion, and then the molded article is removed from the mold. It is then crushed to rupture some of the closed cells to allow at least some air flow. It is now ready to be either glued or otherwise affixed to the seal plate. As shown in FIG. 3 the reactants are first mixed (A), the mixture is introduced into the mold (B), the mixture is caused to foam (C), and the foam is cured (D), and the molded foam is next removed from the mold (E), and the molded foam is then crushed (F).

EXAMPLE 1

Polyol, catalyst, filler, plasticizer, antifoam agent, surfactant and internal mold release agents were premixed at room temperature (see the Table 1 for specific compositions—the owners/sources of the trademarks/-products are listed in Table 2). The material was introduced into a preheated mold at a temperature (about 50° C.) sufficient to cause foaming as part of a two stream introduction of materials (mix/meter machine). The isocyanate was added as the second stream. Cushions were then removed from the mold as quickly as possible to prevent puckering and crushed in order to open some of the as-formed closed cells. The cushion was bonded to the seal plate using conventional pressure sensitive adhesive. The liners were inserted, and the headband attached, all in conventional fashion. Testing was performed with the muff to demonstrate the increased attenuation as discussed below.

TABLE 1

Formulation and Physical Properties for Standard Size Dynamically Stiff Ear Muff Cushion

| Ingredients | 1 | 2 | 3 | 4 | 5 | 6 | 7 | 8 | 9 | 10 | 11 | 12 | 13 |
|---|---|---|---|---|---|---|---|---|---|---|---|---|---|
| LHT-240 | 56.00 | 56.00 | 56.00 | 56.00 | 56.00 | 56.00 | 56.00 | 56.00 | 56.00 | | 34.00 | 34.00 | 56.00 |
| PPG-425 | 12.00 | 12.00 | 12.00 | 12.00 | 12.00 | 12.00 | 12.00 | 12.00 | 12.00 | | 12.00 | 12.00 | 12.00 |
| LG-56 | 12.00 | 12.00 | 12.00 | 12.00 | 12.00 | 12.00 | 12.00 | 12.00 | 12.00 | | 34.00 | 34.00 | 12.00 |
| Niax 11-34 | | | | | | | | | | 100.00 | | | |
| Y-4347 | 3.60 | 3.60 | 3.60 | 3.60 | 3.60 | 3.60 | 3.60 | 3.60 | 3.60 | 1.20 | 3.60 | 3.60 | 3.60 |
| L-45 | 3.60 | 3.60 | 3.60 | 3.60 | 3.60 | 3.60 | 3.60 | 3.60 | 3.60 | 3.60 | 3.60 | 3.60 | 3.60 |
| 1,4 Butanediol | 1.50 | 1.50 | 1.50 | 1.50 | 1.50 | 1.50 | 1.50 | 1.50 | 1.50 | | 1.50 | 1.50 | 1.50 |
| DE83R | 18.60 | 18.60 | 18.60 | 18.60 | 18.60 | 18.60 | | | | | | | |
| Antimony Oxide | 6.20 | 6.20 | 6.20 | 6.20 | 6.20 | 6.20 | | | | | | | |
| Aluminum Trihydrate | 40.00 | 40.00 | 40.00 | 40.00 | 40.00 | 40.00 | | | | | | | |
| Water | 0.79 | 0.79 | 0.79 | 0.79 | 0.79 | | 0.79 | 0.81 | 1.10 | 1.10 | 0.73 | 0.73 | |
| Methylene Chloride | 9.00 | 9.00 | 9.00 | 9.00 | 9.00 | 9.00 | | | | | 9.00 | 9.00 | |
| Ucar 154 | | | | | | 1.98 | | | | | | | 2.75 |
| Tinuvin | 0.60 | 0.60 | 0.60 | 0.60 | 0.60 | 0.60 | 0.60 | 0.60 | 0.60 | | 0.60 | 0.60 | 0.60 |
| T-12 | 0.10 | 0.10 | 0.10 | 0.10 | 0.10 | 0.10 | 0.10 | 0.10 | 0.10 | 0.10 | 0.10 | 0.10 | 0.20 |
| BL-11 | | 0.10 | 0.10 | 0.10 | 0.10 | 0.10 | 0.10 | 0.10 | 0.10 | 0.04 | 0.10 | 0.10 | 0.10 |
| PPG-566 Green | 0.90 | 0.90 | 0.90 | 0.90 | 0.90 | 0.90 | 0.15 | 0.15 | 0.15 | | 0.15 | 0.15 | |
| 83PC03 Brown | | | | | | | | | | 0.25 | | | |
| 27A14 Red | | | | | | | | | | | | | 0.01 |
| Ilsonate 143L | 47.25 | 46.17 | 45.07 | 43.97 | 50.57 | 47.25 | 47.25 | 47.25 | 47.25 | 26.86 | 39.24 | 43.26 | 47.49 |
| Ratio | 3.49 | 3.57 | 3.66 | 3.75 | 3.26 | 3.51 | 1.91 | 1.91 | 1.92 | 3.96 | 2.53 | 2.29 | 1.94 |
| Index | 75.93 | 74.17 | 72.40 | 70.63 | 81.24 | 75.93 | 77.00 | 75.80 | 70.70 | 100.00 | 77.00 | 85.00 | 70.70 |
| Physical Properties: | | | | | | | | | | | | | |
| Height (inches) | 0.669 | 0.662 | 0.654 | 0.662 | 0.701 | 0.651 | 0.673 | 0.662 | 0.655 | 0.656 | 0.654 | 0.662 | 0.660 |
| Density (PCF) | 12.6 | 12.3 | 12.9 | 13.1 | 10.8 | 12.3 | 9.2 | 8.7 | 7.5 | 8.6 | 8.6 | 7.3 | 9.3 |
| Defection, 12N (inches) | 0.051 | 0.123 | 0.154 | 0.240 | 0.049 | 0.084 | 0.079 | 0.172 | 0.352 | 0.025 | 0.026 | 0.081 | 0.282 |
| $F_s$ (lbs/inch) | | 82.7 | 18.3 | 11.7 | 57.7 | 53.5 | 35.6 | 16.4 | | 108.5 | 12.5 | 34.9 | 10.00 |
| Insertion Loss: NRR(dB) | | | | | | | | | | | | | |
| Model 1000 | 24.9 | 25.0 | 25.1 | 24.8 | 25.1 | 24.3 | 24.1 | 24.5 | 23.6 | 17.2 | 22.1 | 23.1 | |
| Model 2000 | 27.3 | 27.0 | 27.0 | 27.6 | 26.2 | | | | | 22.7 | 25.5 | | |
| Model 3000 | 27.7 | 27.7 | 27.8 | 28.9 | 26.2 | 27.7 | 26.3 | 26.9 | | 24.4 | 27.1 | | 29.5 |
| Transmissibility | | | | | | | | | | | | | |
| Fn(Hz) | 300 | 160 | 132 | 132 | 356 | 200 | 212 | 180 | 132 | 60 | 60 | 112 | 156 |
| A or $L_T$(dB) | 4.3 | 30 | 3.1 | 2.8 | 6.2 | 3.8 | 4.1 | 3.7 | 3.5 | 13.9 | 5.7 | 3.8 | 3.1 |
| K* (lbs/inch) | 9187 | 2613 | 1778 | 1779 | 12936 | 4083 | 4588 | 3307 | 1779 | 367 | 367 | 1280 | 2484 |
| $\eta$ | 0.77 | 1.00 | 0.98 | 1.05 | 0.56 | 0.85 | 0.80 | 0.86 | 0.90 | 0.21 | 0.61 | 0.85 | 0.98 |
| Cushion Number | 89A2 | 96A4 | 94B2 | 95C2 | 95D3 | 98A7 | 3B3 | 3C2 | 5A1 | 8B1 | 12C3 | 13A3 | 15A2 |

| | Examples | | | | | | | |
|---|---|---|---|---|---|---|---|---|
| Ingredients | 14 | 15 | 16 | 17 | 18 | 19 | 20 | 21 |
| LHT-240 | 56.00 | 56.00 | 56.00 | 56.00 | 56.00 | 56.00 | 56.00 | |
| PPG-425 | 12.00 | 12.00 | 12.00 | 12.00 | 12.00 | 12.00 | 12.00 | |
| LG-56 | 12.00 | 12.00 | 12.00 | 12.00 | 12.00 | 12.00 | 12.00 | |
| Niax 11-34 | | | | | | | | 100.00 |
| Y-4347 | 3.60 | 3.60 | 3.60 | 3.60 | 3.60 | 3.60 | 3.60 | 3.60 |
| L-45 | 3.60 | 3.60 | 3.60 | 3.60 | 3.60 | 3.60 | 3.60 | 3.60 |
| 1,4 Butanediol | 1.50 | 1.50 | 1.50 | 1.50 | 1.50 | 1.50 | 1.50 | 1.50 |
| DE83R | 18.60 | | 18.60 | 18.60 | 18.60 | 18.60 | 18.60 | |
| Antimony Oxide | 6.20 | | 6.20 | 6.20 | 6.20 | 6.20 | 6.20 | |
| Aluminum Trihydrate | 40.00 | | 40.00 | 40.00 | 40.00 | 40.00 | 40.00 | |
| Water | 0.79 | | 0.79 | 0.79 | 0.79 | 0.79 | 0.79 | 1.10 |

TABLE 1-continued
Formulation and Physical Properties for Standard Size Dynamically Stiff Ear Muff Cushion

| | | | | | | | | |
|---|---|---|---|---|---|---|---|---|
| Methylene Chloride | 9.00 | | 9.00 | 9.00 | 9.00 | 9.00 | 9.00 | |
| Ucar 154 | | 2.75 | | | | | | |
| Tinuvin | 0.60 | 0.60 | 0.60 | 0.60 | 0.60 | 0.60 | 0.60 | |
| T-12 | 0.10 | 0.20 | 0.10 | 0.10 | 0.10 | 0.10 | 0.10 | 0.10 |
| BL-11 | 0.10 | 0.10 | | 0.10 | 0.10 | 0.100 | 0.10 | 0.10 |
| PPG-566 Green | 0.90 | | 0.90 | 0.90 | 0.90 | 0.90 | 0.90 | |
| 83PC03 Brown | | | | | | | | 0.15 |
| 27A14 Red | | 0.01 | | | | | | |
| Isonate 143L | 45.07 | 47.49 | 47.25 | 46.17 | 45.07 | 43.97 | 50.57 | 31.64 |
| Ratio | 3.66 | 1.94 | 3.49 | 3.57 | 3.66 | 3.75 | 3.26 | 3.48 |
| Index | 72.40 | 70.70 | 75.93 | 74.17 | 72.40 | 70.63 | 81.24 | 100.00 |
| Physical Properties: | | | | | | | | |
| Height (inches) | 0.491 | 0.501 | 0.411 | 0.412 | 0.411 | 0.405 | 0.418 | 0.404 |
| Density (PCF) | 13.1 | 8.5 | 12.9 | 14.8 | 15.0 | 15. | 13.4 | 11.7 |
| Defection, 12N (inches) | 0.096 | 0.202 | 0.036 | 0.034 | 0.051 | 0.063 | 0.017 | 0.019 |
| $K_s$ (lbs/inch) | 29.4 | 14.30 | 79.0 | 82.7 | 55.2 | 34.0 | 169.3 | 151.1 |
| Insertion Loss: NRR(dB) | | | | | | | | |
| Model 1000 | 25.3 | 24.6 | 26.2 | 25.8 | 25.3 | 26.4 | 26.4 | 20.7 |
| Model 2000 | 27.7 | 28.0 | 28.5 | 27.8 | 28.3 | 28.3 | 28.3 | 24.6 |
| Model 3000 | 29.1 | 29.7 | 28.7 | 29.5 | 29.5 | 29.3 | 28.8 | |
| Transmissibility | | | | | | | | |
| Fn (Hz) | 164 | 200 | 336 | 324 | 256 | 208 | 504 | 84 |
| A or $L_T$ (dB) | 2.8 | 3.7 | 4.4 | 4.0 | 3.0 | 3.0 | 8.0 | 11.8 |
| K* (lbs/inch) | 2745 | 4083 | 11524 | 10715 | 6689 | 4416 | 25928 | 720 |
| η | 1.05 | 0.86 | 0.76 | 0.81 | 1.00 | 1.00 | 0.43 | 0.27 |
| Cushion Number | 10A3 | 15B5 | 89A6 | 96B1 | 96C2 | 96D2 | 96A2 | 6C2 |

TABLE 2
MATERIALS SOURCE LIST

| BRAND NAME | SOURCE LIST | FUNCTION | EQUIVALENT WEIGHT |
|---|---|---|---|
| Arcol LHT 240 | Arco Chemical | Low MW Triol | 234 |
| Arcol PPG 425 | Arco Chemical | Low MW Diol | 210 |
| Arcol LG 56 | Arco Chemical | Medium MW Triol | 1000 |
| Arcol 11-34 | Arco Chemical | High MW Triol | 1580 |
| Y-4347 | Union Carbide | Cell Stabilizer | — |
| L-45 (350) | Union Carbide | Cell Regulator | — |
| 1,4 Butanediol | GAF | Chain Extender | 45 |
| DE 83R | Great Lakes Chem | Fire Retardant | — |
| Antimony Oxide | Amspec Chemical | Fire Retardant | — |
| Aluminum Trihydrate | Solem Industries | Fire Retardant | — |
| Methylen Chloride | Dow Chemical | Blowing Agent | — |
| Ucar 154 | Union Carbide | Cell Stabilizer | 22.5 |
| Tinuvin 765 | Ciba Geigy | HALS | — |
| Dabco T-12 | Air Products | Catalyst | — |
| Dabco BL-11 | Air Products | Catalyst | — |
| PPG-566 | Dayglo | Colorant | — |
| Stantone 83PC03 | Harwick Chemical | Colorant | — |
| Stantone 27A14 | Harwick Chemical | Colorant | — |
| Isonate 143L | Dow Chemical | Isocyanate | 143 |

EXAMPLES 2-21

Polyol, catalyst, filler, plasticizer, antifoam agent, surfactant and internal mold release agents were premixed and degassed at room temperature. The isocyanate was added thereto, and the mixture degassed once again. The material was poured into a mold at a temperature sufficient to cause foaming (e.g., about 50° C.). The formed cushions were then removed from the mold and processed as set forth in Example 1 above.

Attenuation Testing/Insertion Loss Testing

Attenuation testing and Insertion Loss (IL) testing are conducted in accordance with ASA STD 1-1975 (ANSI S3.19), "Method for the Measurement of Real-Ear Protection of Hearing Protectors and Physical Attenuation of Earmuffs". The artificial flesh supplied for the physical method did not meet the Shore 00 durometer requirement of 20±5 stated in the above procedure. Therefore, an artificial flesh made of silicone rubber was made having a measured Shore durometer of 20, being 0.385 inch thick and having a Knowles Electronic pinna over the microphone center. The pinna was obtained from Industrial Research Products, Inc., a Knowles Company.

Insertion Loss testing employs an artificial test fixture (ATF) having artificial flesh yielding insertion loss results for earmuffs which are similar to those attained using real ear testing at threshold (REAT). When using the ATF it should be remembered that attenuation results for better earmuffs are usually bone conduction limited to 35 dB ± about 2 at 2000 Hz.

The EPA has selected the NRR as a measure of hearing protector's noise reducing capabilities. The range of noise reduction ratings for existing hearing protectors is approximately 0 to 30.

When estimating NRR from IL test results, we used 10 dB and 20 dB for minimum 125 Hz insertion loss values for the E-A-R ® Model 1000 & Model 3000 earmuffs respectively. These values were only required for the normal earmuffs as earmuffs utilizing dynamically stiff cushion yield higher values. Standard deviations of 3.0 are employed in calculating estimated NRRs. This value is typical of measured values.

In several Tables, Q FREQ values are also listed. These values are the frequencies controlling the NRR. This means that changes at this frequency directly effect the NRR while changes at other frequencies may have no effect what-so-ever.

Figure 4:
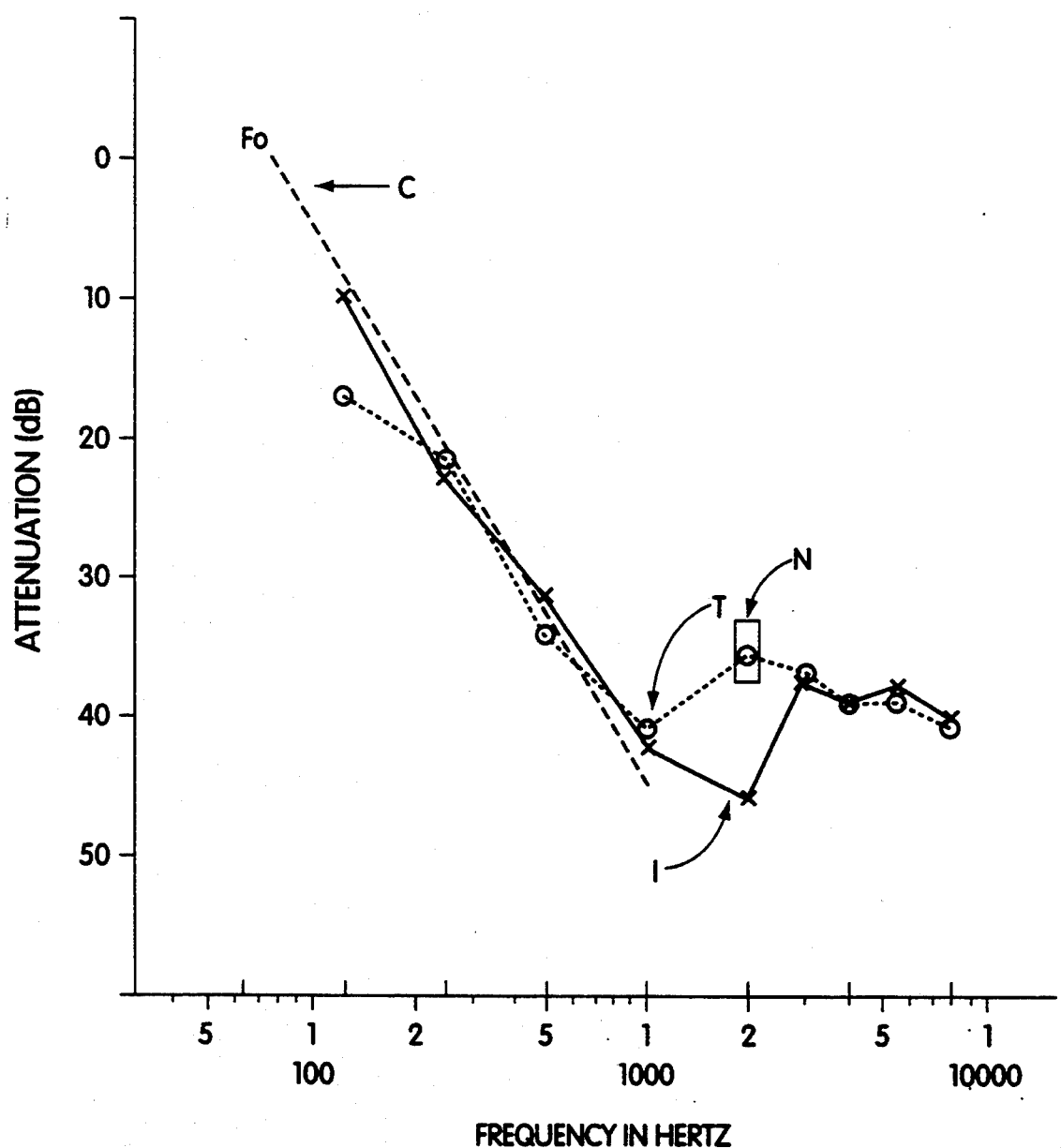
FIGS. 4 and 5 show comparisons of REAT, IL, and calculated attenuation for earmuffs.
Figure 5:
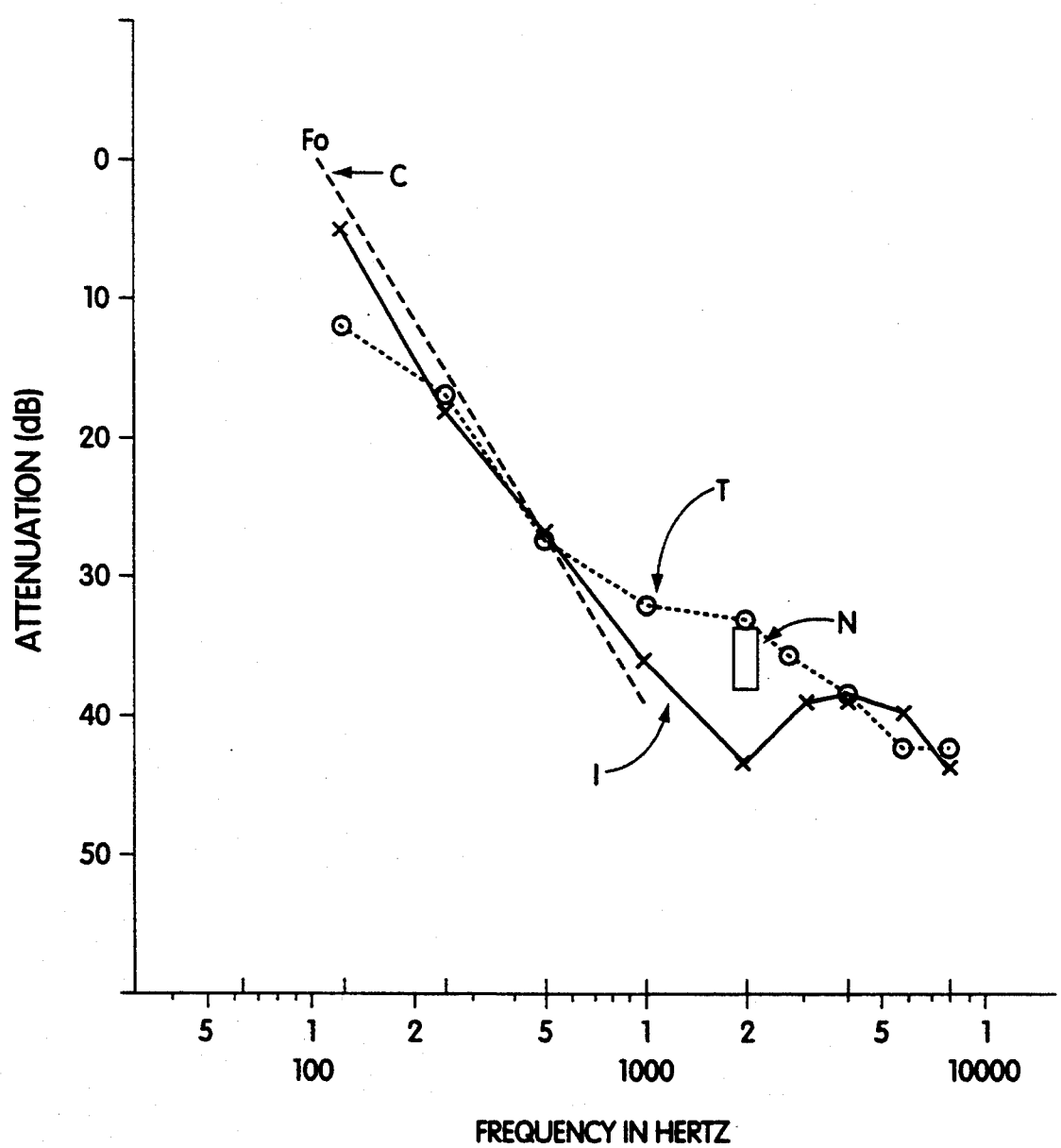

Insertion Loss measurements are only used in lieu of REAT measurements. FIGS. 4 and 5 show comparisons of REAT, IL and calculated attenuation for conventional Model 3000 and Model 1000 Earmuffs respectively. These FIGS. are used as a basis for using IL in lieu of REAT for the purpose of evaluating dynamically stiff cushions.

In FIGS. 4 & 5, C is the calculated value, T is the result of 10 subject test, N is the nominal limit due to bone conduction and I is the insertion loss. The calculated attenuation obtained by determining the frequency at 0 dB Attenuation ($F_O$) using the expression:

$$F_o^2 = A^2/VM \times 35460$$

Where:
A=Area bounded by the cushion outer edge (cm$^2$)
V=Volume (cm$^3$)
M=Mass (gm)

In FIG. 5 the increase in attenuation with frequency is applied using a 12 dB/octave.

Static Deflection Testing

Figure 6:
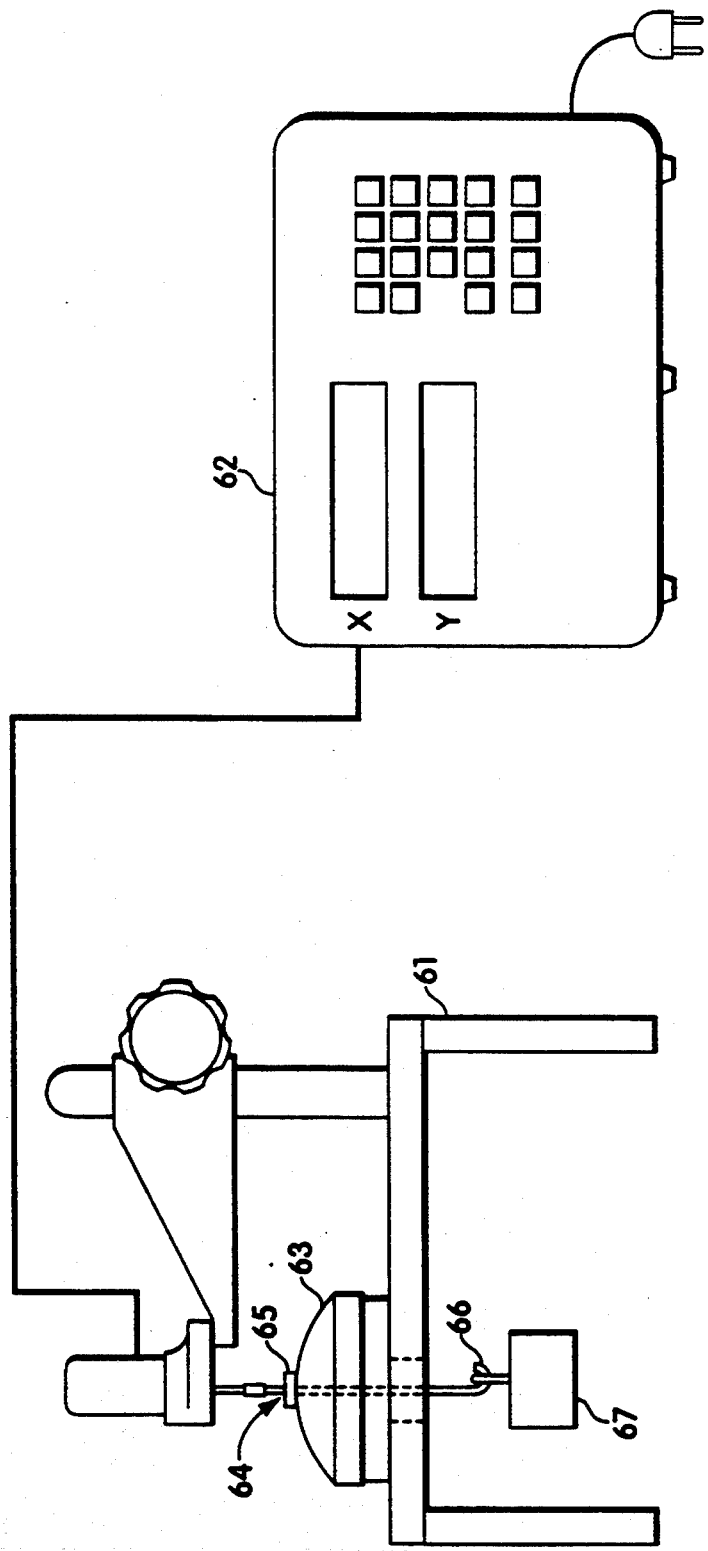
FIG. 6 shows static deflection measuring apparatus.

Static deflection is measured on an apparatus as shown in FIG. 6. The apparatus consists of a platform 61 with an attached adjustable electronic thickness gauge 62. The earmuff cup 63 has a hole 64 at the center of the top. At the top of the hole is a flat plate 65 with attached hook 66 which protrudes through a hole in the platform so as to receive a 12.5 Newton weight 67.

The earmuff cup with cushion in position is placed under the electronic thickness gauge and the gauge is zeroed. Simultaneously to adding a 12.5 Newton weight to the hook a stopwatch is started. After 10 minutes the deflection is read from the electronic thickness gauge and recorded.

In these experiments the earmuff cup employed is from an E-A-R ® Model 1000 Earmuff. The plate cup and hook weighs 90 gms exclusive of the cushion.

Transmissibility Testing

Figure 7:
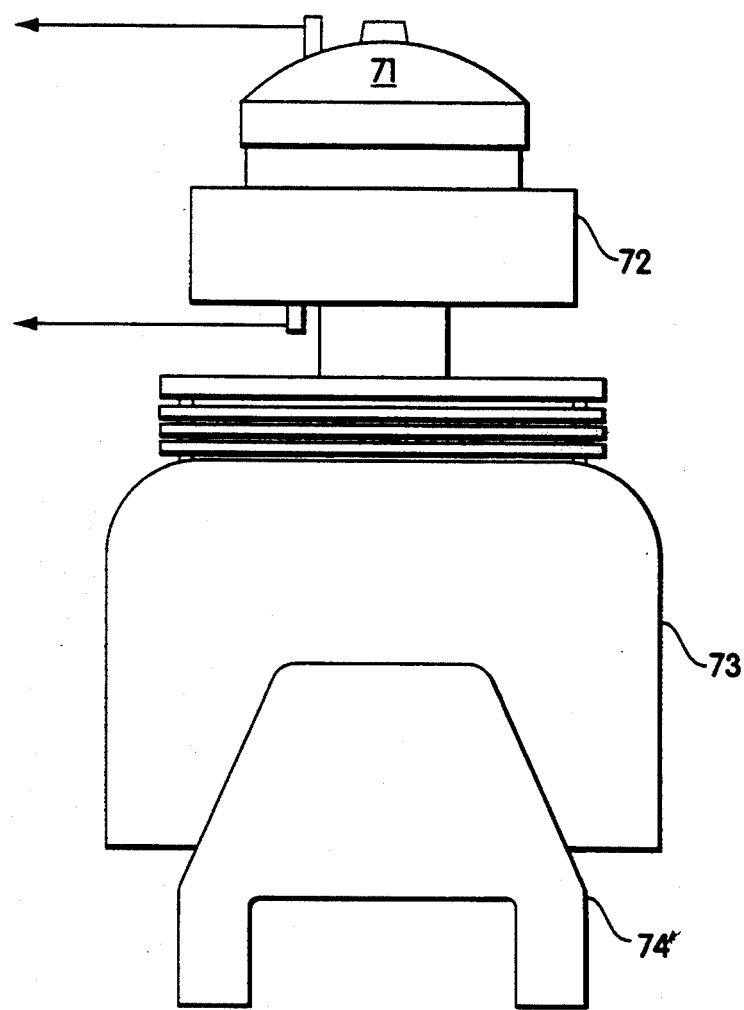
FIG. 7 shows transmissibility measuring apparatus.
Figure 8:
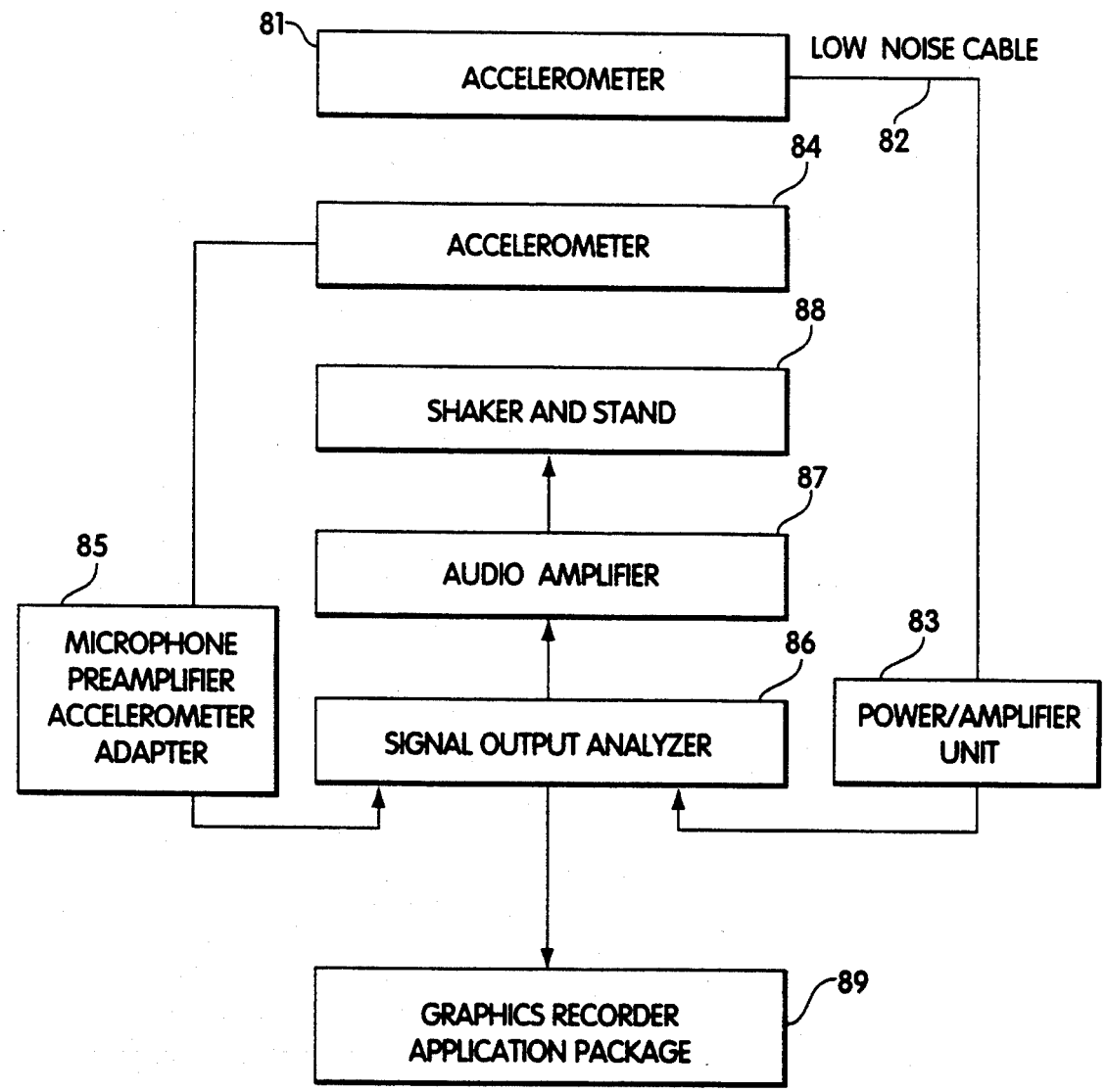
FIG. 8 shows a transmissibility measuring system.

Transmissibility measurements are taken using the fixture shown in FIG. 7 and the equipment shown in the block diagram in FIG. 8.

For this work it was shown that adding weight to the cup to a total weight of 1.00 pound (454 grams) using barium sulfate filled epoxy resin was necessary to ensure adequate contact of the cushion to the platform. This total weight of 1.00 pound was employed during all tests.

Also, adequate stiffness of all connections and of the platform itself must be assured so as to give a straight line output free of secondary resonances to at least 1000 Hz. The platform used in this work was 5.0 inch (12.7 cm) diameter, 1.50 inch (3.81 cm) thick brass.

Figure 9:
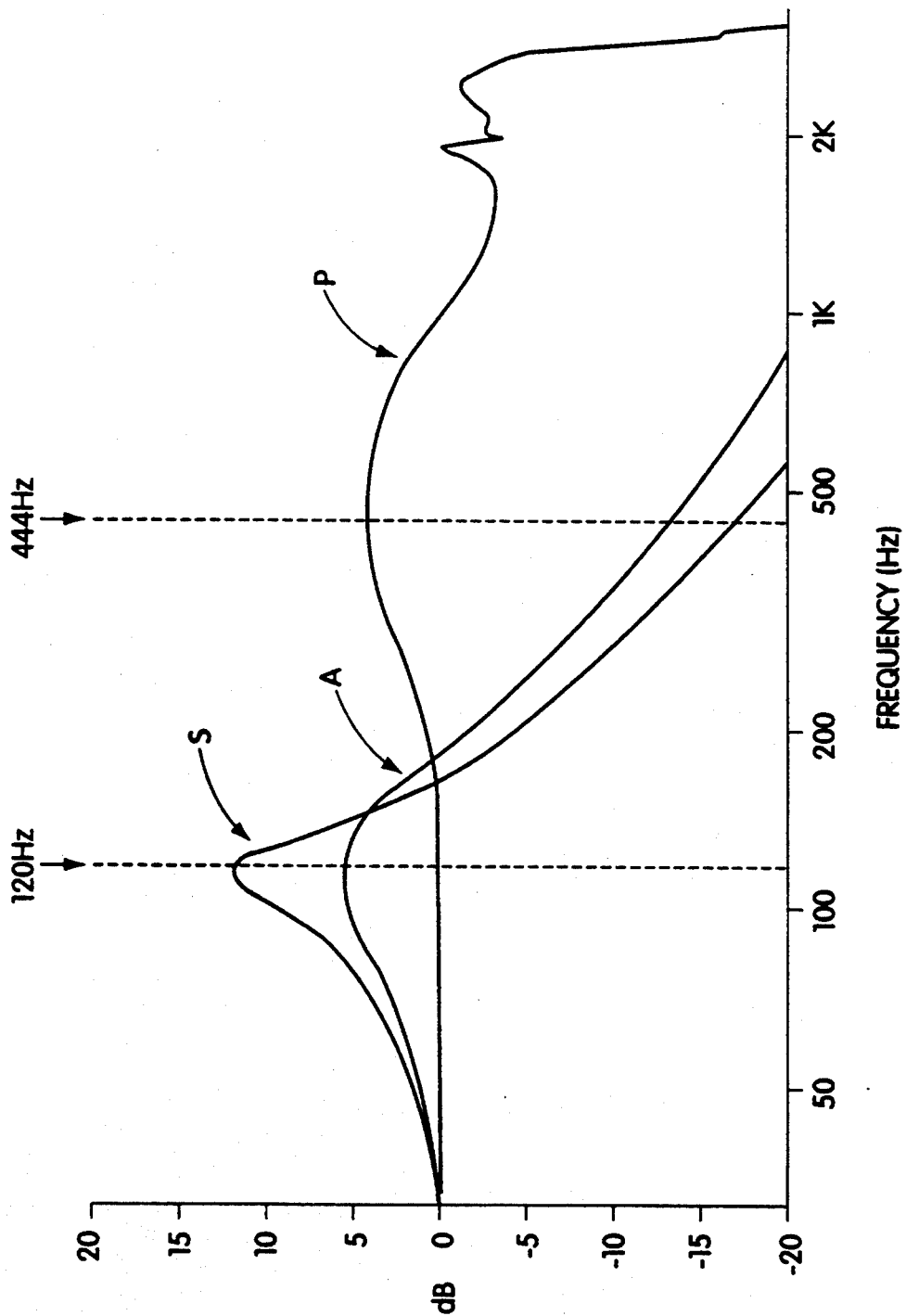
FIG. 9 shows transmissibility tracings for an earmuff.

The test procedure used (with reference to FIGS. 7 and 8) was as follows:

Place the earmuff cup 71 with attached cushion and mass on top of the shaker platform 72. Shaker 73 and stand 74 support the platform. With an input level of 0.2 G (acceleration of gravity, 32 feet/second/second) obtain a transmissibility curve having the cursor at the natural frequency. Read and record the natural frequency (Fn) in Hz and the amplification (A) in dB. In FIG. 8 the accelerometer (81) is connected through the low noise cable (82) to the power/amplifier unit (83). The power/amplifier unit is connected to the signal output analyzer (86) which is connected to the audio amplifier (87) and shaker and stand (88). The accelerometer (84) is connected to the microphone amplifier accelerometer adapter (85) which is also connected to the signal output analyzer. The signal output analyzer is connected to the graphics recorder application package (89). The components are all commercially available, e.g., the accelerometer (81) is a PCB 303A02; the low noise cable is PCB Model PCB 002C05; the power/amplifier is PCB model 40DO6; the low noise cable can also be a PCB 003810; the signal output analyzer is a Bruel and Kjaer Model 30282FFT; the audio amplifier a Proton model D540; the shaker and stand are MB Electronics Model ER1500; the accelerometer (84) is Bruel and Kjaer Model 4693; the microphone preamplifier and accelerometer adapter are Bruel and Kjaer Model 2619 and W/JJ2615 respectively; the graphics recorder and application package are Bruel and Kjaer Model 2313 and W/827006 respectively. The cables are all standard commercially available low noise cables as described above. FIG. 9 shows transmissibility tracings for the E-A-R ® Muff Model 1000 with 3 different cushions. In FIG. 9 the standard is shown by curve S, the Hypol ® urethane/acrylic material is shown by curve A and the polyurethane material of the present invention is shown by curve P. The Fn is directly related to the dynamic complex spring constant (K*) of the cushion and the amplification at resonance (A, sometimes referred to as $L_T$) to the material loss factor. Since the K* and η vary with frequency, the exact weight of 1.00 pound (454gram) must be used to determine these values. K* and η are calculated using the following equations:

$$K^* = ((Fn)^2/3.13)W \text{ lbs./inch } (W = \text{weight in lbs.})$$

$$\eta = 1/(\sqrt{(10^{L_T/20})^2 - 1})$$

where $L_T$=A=level of transmissibility at resonance (dB).

Earmuff Attenuation

Figure 10:
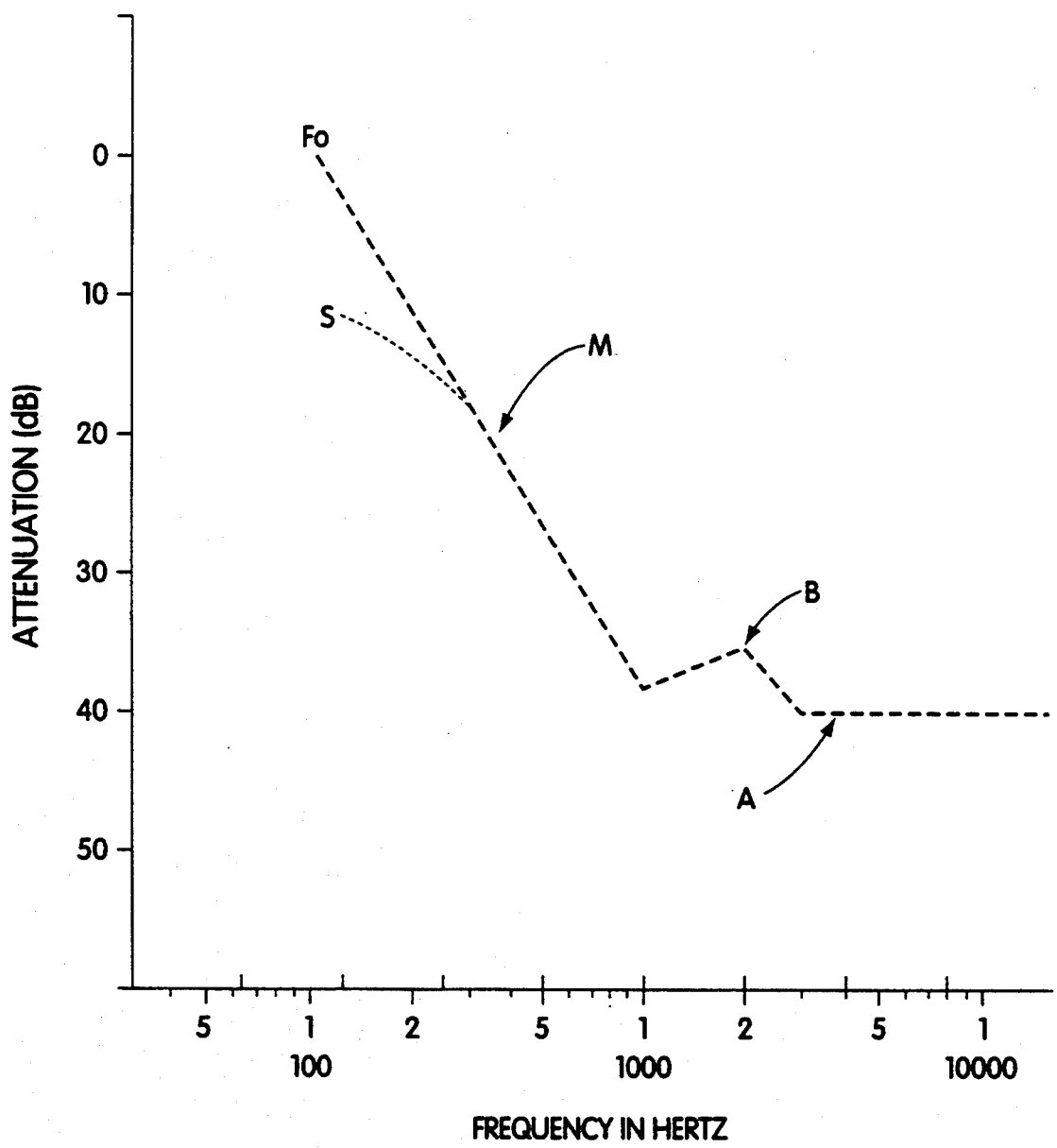
FIG. 10 shows controlling factors for earmuff attenuation.
Figure 11A:
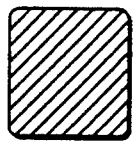
FIG. 11 shows shapes of various earmuffs.
Figure 11B:
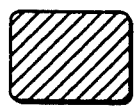
Figure 11C:
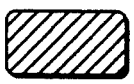
Figure 11D:
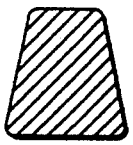
Figure 11E:
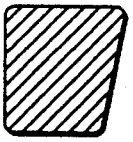
Figure 11F:
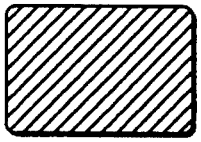
Figure 11G:
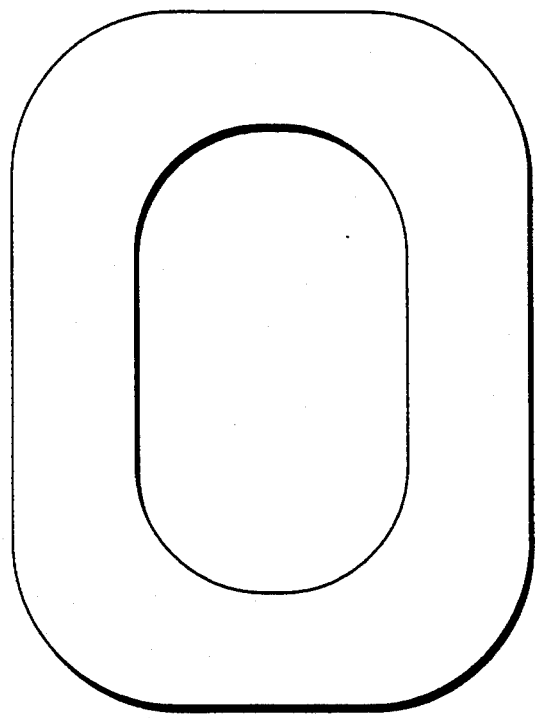
Figure 11H:
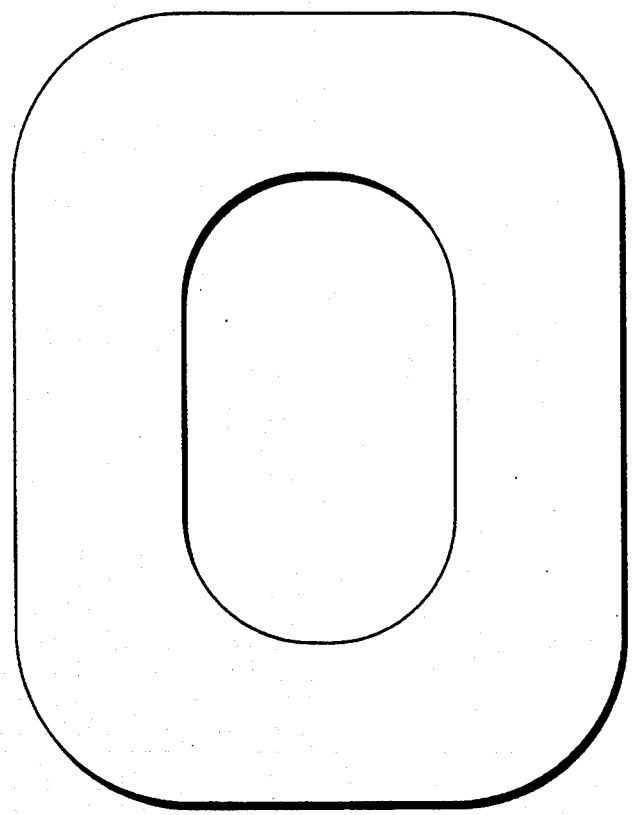

A simplified diagram showing the controlling factors for earmuff attenuation is shown in FIG. 10. Occlusion effect of the cushion/flush stiffness is shown by curve S, the mass by curve M and the bone conduction by limit by B and the stiffness surface area absorption by A. The frequency calculations are as follows:

Low Frequency: $F_o = A/2\pi \sqrt{PC^2/VM}$ : $PC^2/(2\pi)^2 = 35460$

: $F_o^2 = A^2/VM \times 35460$

Where:
$F_o$=Frequency @0 dB attenuation
A=area bounded by the cushion outer edge
V=volume
M=mass P = density of air
C = speed of sound in air At very low frequencies (normally up to 125 or 250 Hz) the cushion/flesh stiffness controls earmuff attenuation.

Additionally, the occlusion effect causes a somewhat higher apparent attenuation at the lower frequencies due to masking by body noise when wearing a hearing protector.

Generally, this low frequency stiffness controlled attenuation is thought to be limited by the low stiffness of the flesh about the ear. Even the cushion stiffness is limited by the balance between wearer comfort and the ability of the cushion to produce an acoustical seal against the head.

The low frequency attenuation from 125 to 1000 Hz can be predicted by calculating the frequency at 0 dB attenuation using the equations as described for FIGS. 4, 5, or 10 and then extrapolating drawing a descending line increasing in attenuation by 12 dB per octave up to 1000 Hz. Above 1000 Hz earmuff attenuation is controlled by the surface area of the cup, absorption within the cup, stiffness of the cup and at some frequencies (notably 2000 Hz) by bone conduction. Bone conduction or body conduction is sound reaching the inner ear by other paths besides directly down the ear canal.

Since earmuffs normally have large attenuation values at frequencies above 1000 Hz, these frequencies yield adequate protection and traditionally have presented little or no problems.

However, much lower attenuation values are attained at frequencies below 1000 Hz, and therefore increases in attenuation within this frequency range can yield significant increases in protection and in the resultant Noise Reduction Rating (NRR).

NOISE REDUCTION RATING (NRR)

The Noise Reduction Rating (NRR), a variant of the NIOSH $R_c$ factor, is the current EPA proposed single number descriptor. The NRR is fully defined in EPA (1979) *Noise Labeling Requirements for Hearing Protectors*, Federal Register, Vol. 42, No. 190, 40 C.F.R. Part 211, 56139–56147. A sample NRR calculation is demonstrated in Table 3. The key point to consider is that the NRR is subtracted from the measured (unprotected) C-weighted sound level to yield an effective A-weighted sound exposure for the employee. The idea of subtracting a noise reduction factor from a C-weighted sound level to find an A-weighted exposure was first proposed by Botsford in 1973. This "C-A concept" is the important common ingredient in all of the successful single number descriptors proposed in recent years. As can be seen in Table 3, the NRR is the difference between the overall C-weighted sound level of a pink (flat by octaves) noise spectrum and resulting A-weighted noise levels under the protector. The attenuation values used in the calculation are the measured laboratory attenuation values minus two standard deviations. This correction assures that the attenuation values used in the calculation procedure are actually realizable by the majority of employees who conscientiously and correctly wear their protectors. This correction will not account for employee misuse or abuse of the protectors.

TABLE 3

| HOW TO CALCULATE THE NRR | | | | | | | |
|---|---|---|---|---|---|---|---|
| OCTAVE BAND REQUENCY (Hz) | 125 | 250 | 500 | 1000 | 2000 | 4000 | 8000 |
| 1. Hypothetical noise spectrum OB sound levels (pink noise) | 100.0 | 100.0 | 100.0 | 100.0 | 100.0 | 100.0 | 100.0 |
| 2. C-weighted OB sound levels unprotected ear | 99.8 | 100.0 | 100.0 | 100.0 | 99.8 | 99.2 | 97.0 |
| | (level assumed is not significant) | | | | | | |
| 3. Overall C-weighted sound level (logarithmic sum of the seven OB sound levels in step 2) | 108.0 dBC | | | | | | |
| 4. A-Weighted OB sound levels unprotected ear | 83.9 | 91.4 | 96.8 | 100.0 | 101.2 | 101.0 | 98.9 |
| 5. E-A-R ® Plug mean attenuation | 29.6 | 31.3 | 34.1 | 34.0 | 35.5 | 41.4* | 39.6** |
| 6. E-A-R ® Plug standard deviations x2 | 6.4 | 6.6 | 4.2 | 4.6 | 5.4 | 3.9* | 4.6* |
| 7. Protected A-weighted OB sound levels (Step 4 - Step 5 + Step 6) | 60.7 | 66.7 | 66.9 | 70.6 | 71.1 | 63.5 | 64.1 |
| 8. Overall A-weighted sound level under the protector (effective exposure) - 76.0 dBA (logarithmic sum of the seven OB sound levels in step 7) | | | | | | | |
| 9. NRR = Step 3 - Step 8 - 3 dB NRR = 108.0–76.0–3 = 29 dB | | | | | | | |

OB-Octave band
This is a correction (safety) factor to protect against over estimating the device's noise reduction because of possible variations in the spectra of actual industrial noises.
*Numerical average of the 3000 Hz and 4000 Hz data.
**Numerical average of the 6000 Hz and 8000 Hz data.

Cushions Shapes & Sizes-vs-Insertion Loss

Dynamically stiff polyurethane foam earmuff cushions of Example 1 were made into various shapes shown in FIGS. 11A through 11H. In FIGS. 11A through 11F the following cushions are shown in cross sections: the standard cushion (A); medium cushion (B); thin cushion (C); tapered cushion (D); reversed taper (E); and large (F). The back plates are shown with all cushions except for large (11G) and for large cushions (11H). The hole in the cushions lines up with the hole in the back plate. The upper portion of each cross section as shown is that normally contacting the head.

Insertion Loss measured values for these shapes are shown in Table 4 with the physical properties listed in Table 5. Of the various shapes as measured on the E-A-R ® Model 1000 Earmuff several conclusions may be drawn:

1. All dynamically stiff cushions are superior to normal Model 1000 cushions with respect to low frequency attenuation and estimated NRR.
2. The Reversed Taper cushions yield the highest low frequency insertion losses and NRR. This cushion is followed by the Thin, Standard and Tapered shapes respectively.
3. The Tapered cushion when inverted so as to give the same area of contact with the head as the Standard cushion gave similar results.
4. Crushing the foam cushion had no significant effect on Insertion Loss.
5. The Reversed Taper, Thin and Large cushions all yielded higher high frequency insertion loss.

TABLE 4

INSERTION LOSS MEASUREMENTS USING DIFFERENT EARMUFF CUSHION SHAPES OF DYNAMICALLY STIFF FOAM - EXAMPLE 1

| Earmuff | Cushion/Example | 125 | 250 | 500 | 1000 | 2000 | 3150 | 4000 | 6300 | 8000 | NRR Est. (db) | Q Freq. |
|---|---|---|---|---|---|---|---|---|---|---|---|---|
| Model 1000 | Normal | 4.0 | 17.1 | 25.8 | 35.1 | 42.4 | 38.4 | 37.5 | 39.2 | 42.9 | 20.7 | 250 |
| Model 1000 | Std. | 19.8 | 21.5 | 30.8 | 34.3 | 45.8 | 37.2 | 34.3 | 35.3 | 39.8 | 25.0 | 250 |
| Model 1000 | Std. - High Wt. | 20.4 | 22.0 | 31.0 | 34.7 | 44.8 | 36.0 | 34.7 | 36.4 | 41.0 | 25.3 | 250 |
| Model 1000 | Tapered | 16.3 | 20.0 | 30.0 | 37.8 | 44.0 | 35.7 | 33.9 | 35.4 | 38.8 | 23.9 | 250 |
| Model 1000 | Thin | 19.6 | 22.4 | 31.0 | 35.8 | 45.8 | 42.6 | 41.1 | 40.0 | 41.4 | 26.2 | 250 |
| Model 1000 | Large | 20.5 | 21.3 | 29.6 | 32.1 | 45.6 | 38.4 | 38.4 | 39.3 | 42.1 | 24.7 | 250 |
| Model 1000 | Std - Crushed | 20.5 | 21.7 | 31.4 | 34.7 | 44.8 | 35.0 | 34.0 | 38.4 | 40.9 | 25.2 | 250 |
| Model 1000 | Taper - Inverted | 20.2 | 21.3 | 30.9 | 35.3 | 43.4 | 34.3 | 33.2 | 38.1 | 41.0 | 24.9 | 250 |
| Model 1000 | Std - Crushed + ¼" 3002 | 18.4 | 21.1 | 31.8 | 34.7 | 43.3 | 30.7 | 32.0 | 37.9 | 39.5 | 24.0 | 250 |
| Model 1000 | Reverse Taper | 24.0 | 24.0 | 30.1 | 34.5 | 47.8 | 39.0 | 36.3 | 40.2 | 42.3 | 26.5 | 250 |
| Model 3000 | Normal | 9.8 | 22.8 | 32.0 | 41.6 | 45.4 | 36.8 | 38.3 | 37.8 | 39.3 | 26.7 | 250 |
| Model 3000 | Std. | 25.0 | 25.3 | 35.0 | 36.2 | 46.8 | 29.5 | 33.5 | 35.5 | 38.4 | 26.1 | 3/4K |
| Model 3000 | Std. - High Wt. | 24.5 | 26.5 | 35.5 | 37.5 | 43.5 | 33.3 | 35.4 | 35.8 | 38.8 | 27.6 | 3/4K |
| Model 3000 | Tapered | 21.4 | 24.3 | 34.8 | 40.5 | 45.5 | 30.3 | 34.8 | 35.1 | 37.0 | 26.3 | 3/4K |
| Model 3000 | Thin | 25.5 | 25.6 | 35.7 | 38.0 | 45.7 | 37.4 | 37.8 | 39.5 | 39.0 | 28.7 | 250 |
| Model 3000 | Large | 24.8 | 25.4 | 34.7 | 36.4 | 47.2 | 31.1 | 34.5 | 35.6 | 39.7 | 26.7 | 3/4K |
| Model 3000 | Large - No BP | 23.8 | 25.8 | 35.5 | 34.7 | 45.8 | 31.4 | 34.9 | 37.2 | 39.4 | 26.7 | 3/4K |
| Model 3000 | Reverse Taper | 27.0 | 27.0 | 34.7 | 37.7 | 45.3 | 35.0 | 37.5 | 36.8 | 39.2 | 28.5 | 3/4K, 250 |
| Model 1000 | Normal | 4.0 | 17.7 | 25.8 | 35.1 | 42.4 | 38.4 | 37.5 | 39.2 | 42.9 | 20.7 | 250 |
| Model 1000 | Thin/2 | 20.7 | 22.0 | 32.5 | 35.5 | 43.5 | 41.3 | 40.7 | 41.8 | 43.3 | 26.4 | 250 |
| Model 1000 | Thin/17 | 18.3 | 22.4 | 31.7 | 34.0 | 42.7 | 42.2 | 42.3 | 42.0 | 43.2 | 25.8 | 250 |
| Model 1000 | Thin/18 | 18.8 | 21.2 | 30.5 | 34.2 | 44.3 | 42.0 | 41.7 | 41.7 | 43.1 | 25.3 | 250 |
| Model 1000 | Thin/19 | 18.7 | 21.3 | 30.5 | 35.0 | 43.8 | 41.0 | 41.8 | 41.8 | 43.2 | 25.4 | 250 |
| Model 1000 | Thin/6 | 19.6 | 21.6 | 32.0 | 33.3 | 41.1 | 40.8 | 40.7 | 41.7 | 42.9 | 25.5 | 250 |
| Model 1000 | Thin/6 (Crushed) | 20.5 | 20.5 | 31.6 | 35.6 | 42.8 | 41.5 | 40.8 | 41.3 | 43.1 | 25.4 | 250 |
| Model 3000 | Normal | 9.8 | 22.8 | 32.0 | 41.6 | 45.4 | 36.8 | 38.3 | 37.8 | 39.3 | 26.7 | 250 |
| Model 3000 | Thin/2 | 25.2 | 27.8 | 36.1 | 36.0 | 43.5 | 39.4 | 36.0 | 38.8 | 38.7 | 38.8 | 1K/250 3 + 4K |
| Model 3000 | Thin/17 | 26.0 | 26.8 | 35.8 | 38.8 | 46.3 | 40.7 | 37.0 | 39.2 | 39.0 | 29.5 | 250 |
| Model 3000 | Thin/18 | 25.7 | 26.3 | 35.9 | 40.0 | 46.5 | 40.7 | 37.8 | 38.9 | 39.2 | 29.5 | 250 |
| Model 3000 | Thin/19 | 25.2 | 26.1 | 35.5 | 38.3 | 46.5 | 41.5 | 38.3 | 39.1 | 39.7 | 29.3 | 250 |
| Model 3000 | Thin/6 | 25.8 | 27.0 | 35.8 | 37.3 | 45.7 | 40.6 | 37.1 | 39.0 | 39.2 | 29.2 | 250 |
| Model 2000 | Thin/2[1] | 24.6 | 24.0 | 33.7 | 36.5 | 44.0 | 39.1 | 35.5 | 37.8 | 40.0 | 27.4 | 250 |
| Model 2000 | Thin/2[2] | 23.6 | 24.6 | 34.4 | 36.6 | 45.3 | 42.3 | 38.3 | 38.5 | 39.0 | 28.0 | 250 |
| Model 2000 | Thin/2[3] | 24.3 | 24.7 | 33.7 | 36.1 | 45.3 | 43.8 | 41.0 | 40.0 | 42.1 | 28.3 | 250 |
| Model 2000 | Thin/17[3] | 23.3 | 23.8 | 33.2 | 36.3 | 46.4 | 44.3 | 41.1 | 40.5 | 42.0 | 27.8 | 250 |
| Model 2000 | Thin/18[3] | 23.5 | 24.7 | 33.4 | 36.3 | 47.2 | 44.5 | 41.0 | 41.1 | 42.5 | 28.3 | 2500 |
| Model 2000 | Thin/19[4] | 21.6 | 23.0 | 33.0 | 37.4 | 47.9 | 36.0 | 34.3 | 29.1 | 33.4 | 25.4 | 250/6 + 8 |
| Model 2000 | Thin/19[3] | 23.1 | 24.3 | 33.2 | 37.4 | 47.1 | 44.5 | 42.5 | 41.0 | 42.8 | 28.3 | 250 |
| Model 2000 | Thin/19[2] | 21.8 | 24.3 | 33.7 | 37.6 | 47.7 | 43.3 | 39.3 | 39.0 | 41.0 | 28.0 | 250 |
| Model 2000 | Thin/19[1] | 22.0 | 24.0 | 33.7 | 37.8 | 46.3 | 41.6 | 38.9 | 40.2 | 40.0 | 27.9 | 250 |
| Model 3000 | Thin/18[5] | 24.8 | 27.0 | 36.0 | 39.7 | 48.0 | 42.0 | 37.3 | 40.2 | 41.0 | 29.9 | 250 |
| Model 3000 | Thin/18[4] | 24.3 | 26.1 | 36.0 | 40.3 | 41.6 | 35.5 | 30.7 | 28.7 | 29.7 | 25.4 | 6 + 8K |
| Model 1000 | Std./2 | 18.8 | 21.7 | 31.7 | 33.6 | 43.6 | 36.5 | 34.8 | 39.4 | 42.0 | 25.0 | 250 |
| Model 1000 | Std./3 | 18.0 | 21.6 | 31.7 | 34.4 | 43.8 | 37.8 | 35.3 | 38.7 | 42.8 | 25.1 | 250 |
| Model 1000 | Std./4 | 17.3 | 20.6 | 30.2 | 36.5 | 44.3 | 38.7 | 37.5 | 41.8 | 43.9 | 24.8 | 250 |
| Model 1000 | Std./5 | 20.1 | 23.0 | 32.1 | 33.3 | 43.4 | 32.8 | 33.5 | 37.1 | 40.4 | 25.1 | 250/3 + 4K |
| Model 1000 | Std./7 | 19.7 | 20.5 | 31.0 | 33.1 | 43.7 | 34.2 | 33.0 | 37.1 | 40.2 | 24.1 | 250 |
| Model 1000 | Std./6 | 19.0 | 20.0 | 30.1 | 34.5 | 45.0 | 37.1 | 35.5 | 38.3 | 42.3 | 24.3 | 250 |
| Model 1000 | Std./8 | 19.4 | 19.8 | 30.5 | 35.8 | 44.0 | 37.9 | 35.8 | 38.5 | 42.0 | 24.5 | 250 |
| Model 1000 | Std./9 | 16.4 | 19.0 | 29.8 | 37.2 | 43.3 | 36.5 | 34.4 | 38.1 | 41.8 | 23.6 | 250 |
| Model 3000 | Std./2 | 24.3 | 26.1 | 35.0 | 39.3 | 47.6 | 33.2 | 34.3 | 38.0 | 39.0 | 27.7 | 3 + 4K |
| Model 3000 | Std./3 | 24.0 | 25.7 | 35.0 | 39.7 | 47.5 | 34.2 | 34.8 | 38.2 | 38.7 | 27.8 | 3 + 4K/250 |
| Model 3000 | Std./4 | 22.7 | 26.4 | 35.0 | 40.5 | 48.1 | 37.9 | 36.8 | 39.7 | 46.2 | 28.9 | 250/3 + 4K |
| Model 3000 | Std./5 | 26.0 | 27.6 | 36.0 | 37.0 | 46.4 | 29.5 | 32.0 | 34.9 | 37.3 | 26.2 | 3 + 4K |
| Model 3000 | Std./6 | 24.8 | 26.4 | 35.4 | 38.8 | 47.6 | 33.5 | 33.8 | 37.4 | 38.3 | 27.7 | 3 + 4K |
| Model 3000 | Std./7 | 24.6 | 26.8 | 35.8 | 38.4 | 47.6 | 30.5 | 31.5 | 34.8 | 36.8 | 26.3 | 3 + 4K |
| Model 3000 | Std./8[5] | 23.6 | 27.1 | 35.7 | 39.8 | 47.9 | 32.1 | 31.6 | 36.2 | 37.0 | 26.9 | 3 + 4K |
| Model 2000 | Std./2 | 21.7 | 24.3 | 32.7 | 37.0 | 47.5 | 36.8 | 34.8 | 38.2 | 40.7 | 27.0 | 250 |
| Model 2000 | Std./3 | 20.6 | 24.7 | 32.5 | 37.1 | 46.9 | 36.8 | 35.3 | 38.0 | 41.0 | 27.0 | 250 |
| Model 2000 | Std./4 | 20.1 | 24.3 | 33.1 | 38.0 | 47.2 | 39.5 | 38.0 | 40.7 | 42.8 | 27.6 | 250 |

TABLE 4-continued

INSERTION LOSS MEASUREMENTS USING DIFFERENT EARMUFF CUSHION SHAPES
OF DYNAMICALLY STIFF FOAM - EXAMPLE 1

Insertion Loss (dB)

| Earmuff | Cushion/Example | 125 | 250 | 500 | 1000 | 2000 | 3150 | 4000 | 6300 | 8000 | NRR Est. (db) | Q† Freq. |
|---|---|---|---|---|---|---|---|---|---|---|---|---|
| Model 2000 | Std./5 | 24.2 | 25.5 | 34.2 | 34.3 | 47.3 | 32.4 | 32.5 | 35.8 | 38.5 | 26.2 | 3 + 4K |
| Model 2000 | Std./1[6] | 20.9 | 25.2 | 33.8 | 39.1 | 46.3 | 36.4 | 34.6 | 36.5 | 38.5 | 27.3 | 250/3 + 4K |
| Model 2000 | Std./16 | 22.1 | 25.0 | 33.8 | 35.3 | 46.7 | 33.9 | 33.0 | 36.5 | 38.9 | 26.4 | 3 + 4K/250 |
| Model 2000 | Thin/1&16 | 23.3 | 25.2 | 33.8 | 36.1 | 47.0 | 44.6 | 41.8 | 40.4 | 42.4 | 28.5 | 250 |
| Model 2000 | Std./1[7] | 22.8 | 24.9 | 33.1 | 36.4 | 47.9 | 33.0 | 32.3 | 35.0 | 39.0 | 26.2 | 3 + 4K |
| Model 2000 | Thin/21 | 15.2 | 22.1 | 28.1 | 40.3 | 40.0 | 40.0 | 39.2 | 38.3 | 42.8 | 24.6 | 250 |
| Model 1000 | Std./1[6] | 18.7 | 21.3 | 31.0 | 34.8 | 44.9 | 36.1 | 35.0 | 38.0 | 41.3 | 24.9 | 250 |
| Model 1000 | Std./1[7] | 19.8 | 21.7 | 31.3 | 33.8 | 44.6 | 35.0 | 33.6 | 37.3 | 40.0 | 24.9 | 250 |
| Model 1000 | Thin/21 | 12.1 | 18.5 | 27.0 | 27.7 | 35.5 | 37.5 | 37.3 | 40.0 | 43.0 | 20.7 | 250/1K |
| Model 2636140 | Bulbous | 17.0 | 23.6 | 29.1 | 29.7 | 34.4 | 23.8 | 24.7 | 32.7 | 34.3 | 19.8 | 3 + 4K |
| Model 1000 | Medium/14 | 19.3 | 20.3 | 30.7 | 35.5 | 45.4 | 42.4 | 39.0 | 39.9 | 42.9 | 25.1 | 250 |
| Model 1000 | Medium/14* | 19.9 | 20.4 | 30.5 | 35.3 | 46.3 | 42.3 | 38.4 | 36.8 | 40.3 | 25.0 | 250 |
| Model 2000 | Medium/14 | 21.3 | 22.7 | 33.3 | 37.9 | 47.2 | 40.3 | 34.8 | 38.2 | 41.0 | 26.8 | 250 |
| Model 2000 | Medium/14* | 22.3 | 23.7 | 32.8 | 38.3 | 46.7 | 42.8 | 38.7 | 39.8 | 43.0 | 27.8 | 250 |
| Model 3000 | Medium/14 | 24.3 | 25.8 | 35.1 | 39.5 | 47.1 | 36.7 | 38.3 | 38.4 | 41.2 | 28.8 | 250 |
| Model 3000 | Medium/14* | 24.4 | 27.3 | 35.0 | 40.0 | 47.0 | 40.8 | 37.7 | 38.0 | 39.9 | 29.6 | 250 |
| Model 1000 | Medium/14 | 19.9 | 20.7 | 29.8 | 37.3 | 45.4 | 42.9 | 39.1 | 38.1 | 41.8 | 25.3 | 250 |
| Model 1000 | Medium/14* | 20.1 | 20.8 | 30.4 | 37.8 | 45.7 | 43.0 | 38.9 | 37.3 | 41.0 | 25.5 | 250 |
| Model 1000 | Medium/14** | 20.1 | 20.6 | 30.2 | 36.3 | 45.9 | 43.0 | 39.7 | 38.8 | 42.0 | 25.3 | 250 |
| Model 2000 | Medium/14** | 23.2 | 23.0 | 32.4 | 38.9 | 47.9 | 44.7 | 40.3 | 40.7 | 43.1 | 27.7 | 250 |
| Model 3000 | Medium/14** | 24.7 | 25.3 | 35.9 | 39.8 | 47.1 | 41.6 | 37.8 | 38.6 | 40.0 | 29.1 | 250 |
| Model 1000 | Std./10 | 6.6 | 16.0 | 22.5 | 23.7 | 34.7 | 32.4 | 26.0 | 29.4 | 38.5 | 17.2 | 1000 |
| Model 1000 | Thin/10 | 9.7 | 18.0 | 27.2 | 34.3 | 32.8 | 37.3 | 26.5 | 33.8 | 39.4 | 20.5 | 125 |
| Model 1000 | Thin/12 | 18.7 | 19.7 | 29.0 | 38.8 | 44.7 | 41.0 | 38.3 | 36.6 | 39.8 | 24.5 | 250 |
| Model 1000 | Std./12 | 15.8 | 19.7 | 28.0 | 38.0 | 41.2 | 37.1 | 31.6 | 31.6 | 38.3 | 23.1 | 250 |
| Model 1000 | Thin/11 | 14.2 | 17.5 | 28.0 | 40.0 | 44.4 | 41.4 | 37.9 | 38.6 | 41.7 | 22.5 | 250 |
| Model 1000 | Std./11 | 13.0 | 17.8 | 27.3 | 38.6 | 40.8 | 38.8 | 32.7 | 33.0 | 40.3 | 21.9 | 250 |
| Model 1000 | Std./10** | 6.3 | 14.8 | 23.0 | 24.2 | 35.8 | 32.4 | 26.3 | 28.6 | 39.3 | 17.1 | 250 |
| Model 1000 | Std./11** | 11.7 | 18.8 | 27.7 | 37.8 | 42.5 | 39.6 | 34.6 | 35.8 | 41.6 | 22.1 | 250 |
| Model 2000 | Std./11** | 15.4 | 23.0 | 30.3 | 40.5 | 45.5 | 40.3 | 36.6 | 38.5 | 42.5 | 25.5 | 125/250 |
| Model 3000 | Std./11** | 17.5 | 25.0 | 33.2 | 41.8 | 47.0 | 38.2 | 35.5 | 37.4 | 39.2 | 27.1 | 125/250 |
| Model 1000 | Medium/14** | 19.7 | 19.9 | 29.8 | 36.8 | 45.3 | 42.2 | 39.0 | 38.1 | 41.8 | 24.8 | 250 |
| Model 1000 | Thin/10** | 10.2 | 17.0 | 25.4 | 36.0 | 33.8 | 37.3 | 36.0 | 33.6 | 40.0 | 20.1 | 250 |
| Model 2000 | Thin/10** | 12.0 | 20.7 | 28.2 | 38.1 | 36.5 | 39.0 | 34.7 | 34.4 | 41.7 | 22.7 | 125 |
| Model 3000 | Thin/10** | 13.5 | 23.7 | 31.8 | 39.4 | 28.2 | 36.1 | 33.0 | 34.8 | 39.3 | 24.4 | 125 |
| Model 3000 | Thin/10** | 27.4 | 27.5 | 36.0 | 38.7 | 45.5 | 41.6 | 37.2 | 38.0 | 39.8 | 29.8 | 250 |
| Model 3000 | Medium/15 | 25.0 | 26.7 | 36.7 | 39.3 | 47.5 | 38.5 | 35.7 | 37.6 | 36.8 | 29.0 | 250 |
| Model 2000 | Medium/15 | 22.2 | 24.1 | 33.0 | 38.4 | 47.9 | 42.2 | 38.0 | 38.3 | 40.3 | 27.8 | 250 |
| Model 1000 | Medium/15 | 19.6 | 21.3 | 30.1 | 36.5 | 46.2 | 41.7 | 38.0 | 37.6 | 38.8 | 25.5 | 250 |
| Model 3000 | Medium/15** | 24.4 | 26.2 | 36.0 | 40.5 | 48.3 | 43.6 | 39.8 | 37.8 | 39.2 | 29.7 | 250 |
| Model 2000 | Medium/15** | 21.5 | 23.5 | 32.8 | 40.7 | 49.4 | 45.6 | 43.6 | 40.6 | 40.8 | 28.0 | 250 |
| Model 1000 | Medium/15** | 18.3 | 19.5 | 30.2 | 38.2 | 47.7 | 42.5 | 38.7 | 38.8 | 39.7 | 24.6 | 250 |
| Model 3000 | Std./15 | 25.0 | 28.0 | 36.3 | 40.2 | 48.8 | 34.0 | 34.7 | 35.4 | 37.2 | 28.3 | 3 + 4K |
| Model 3000 | Std./15*** | 25.8 | 28.5 | 36.7 | 41.8 | 49.7 | 36.0 | 35.6 | 36.6 | 38.3 | 29.4 | 3 + 4K |

† Freq. is the frequency in Hz controlling the NRR
[1]Normal Acoustical Foam
[2]1 Piece S1F 110 Foam
[3]2 Pieces S1F 110 Foam
[4]No Acoustical Foam
[5]Damped
[6]Shiney Surface
[7]Coated
*Foamex S1F 110 (1 Piece - Model 1000) (2 Pieces Models 2000/3000)
**Crushed
***Ave. 2nd & 3rd Fitting

TABLE 5

PHYSICAL PROPERTIES OF DYNAMICALLY STIFF CUSHIONS
HAVING DIFFERENT SHAPES & SIZES - EXAMPLE 1

| NO | TYPE | WT (GM) | AV. THICKNESS (IN.) | TOTAL CUSHION OUTER AREA (IN$^2$) | ACTUAL CUSHION AREA (-HOLE) (IN$^2$) | VOL (IN$^3$) | DENSITY (#/FT) |
|---|---|---|---|---|---|---|---|
| 1 | Standard | 14.4888 | 0.671 | 10.126 | 6.543 | 4.390 | 12.6 |
| 1 | Large | 27.7078 | 0.683 | 14.891 | 11.513 | 7.863 | 13.4 |
| 20 | Standard High Wt. | 18.3624 | 0.680 | 10.425 | 6.767 | 4.602 | 15.2 |
| 31 | Thin | 9.5243 | 0.411 | 10.396 | 6.829 | 2.807 | 12.9 |
| 34 | Tapered | 12.7235 | 0.663 | Top 8.812 Btm. 10.095 | Top 4.576 Btm. 6.677 | 3.730 | 13.0 |
| 1 | Rev. Taper | 16.7328 | 0.655 | Top 11.900 | Top 8.371 | 5.023 | 12.7 |

TABLE 5-continued

PHYSICAL PROPERTIES OF DYNAMICALLY STIFF CUSHIONS HAVING DIFFERENT SHAPES & SIZES - EXAMPLE 1

| NO | TYPE | WT (GM) | AV. THICKNESS (IN.) | TOTAL CUSHION OUTER AREA (IN$^2$) | ACTUAL CUSHION AREA (-HOLE) (IN$^2$) | VOL (IN$^3$) | DENSITY (#/FT) |
|----|------|---------|---------------------|------------------------------------|---------------------------------------|--------------|----------------|
|    |      |         |                     | Btm. 10.651                        | Btm. 6.965                            |              |                |

Of the various shapes as measured on the E-A-R ® Model 3000 earmuff, a somewhat different conclusion may be drawn. All dynamically stiff cushions are superior to normal Model 3000 cushions for low frequency Insertion Loss but many shapes do not result in higher estimated NRRs. The Reverse Taper and Thin cushions are exceptions. The rest of the shapes end up with the ¾K Hz frequencies controlling the NRR and limiting further increase. Later experiments will utilize an optimized foam liner to further increase high frequency insertion loss. A total of 14 formulations have been made into earmuff cushions (See Table 1). Five of these formulations Examples 1 through 5 are a series having high filler (flame retardant) concentrations being from softest to hardest respectively. Test results of this series has been broken our in Tables 6 and 7 respectively. The remaining formations have changes as follows:

| FORMULATION-Example | CHANGE |
|---------------------|--------|
| 6, 15, 1            | Water added as part of Latex, UCAR |
| 7, high index       | Filler & MeCl omitted, low water |
| 8, med. index       | Filler & MeCl omitted, med. water |
| 9, low index        | Filler & MeCl omitted, high water |
| 21                  | High Mw Polyol and 100% index |
| 10, 1,4 butanediol  | High Mw Polyol and 100% index, drop |
| 11                  | Increase conc. of high Mw Polyol, Decrease low MW Polyol of 3B |
| 12                  | Same as 12C but increased index |
| 11/12               | No filler or MeCl, water added as UCAR 154, index as 95C, softest |

Of the above formulations the soft to hard series of 5 formulations are aimed at producing a cushion in Standard or Thin cross-section which may help to define the upper limit of suitability for hardness i.e. lowest static deflection.

Example formulations 21, 10, 11 and 12 are aimed at producing cushions helping to define the lower limit of suitable dynamic stiffness.

The remaining formulations are aimed at producing a series of lower density material allowing greater definition of preferred physical characteristics. Table 8 list the Shore 00 Durometers of the various cushions at 7° C., 22° C. and 41° C. This data is given as an alternate measure of hardness to aid those more familiar with this measure.

Equipment

Although most of the formulation were mixed in the laboratory for expedience of changing formations, some cushions were produced using a conventional mix/meter machine (e.g., Edge Sweets Foam Machine Model Flex-2H, Grand Rapids, Mich.). When using the foam machine it was discovered that cushions should be made, colored and/or coated for much less than by employing the processes used to make virtually all of the noise excluding earmuffs on the market today.

Currently commercial earmuff cushions are made using a minimum of two thin sheets of polyvinylchloride or polyurethane, one of which is vacuum formed and filled with a cut-out donut of foam or a liquid followed by thermal bonding and cutting off the trim. Because of the low volumes normally employed, the process is labor intense, results in considerable waste and is costly.

Table 1 show the formulatory and summary physical properties for Standard, Medium and Thin sixed dynamically stiff earmuff cushions respectively. Units are grams (and represent ratios as well).

Table 4 shows the individual insertion loss values as measured and are mostly used as supporting information for Table 1.

Tables 6 and 7 break out the physical properties for the series of five cushions varying from softest to hardest. These data show the Thin cushions to have least static deflection, higher calculated NRRs and higher system natural frequencies (Fn).

The system natural frequencies (Fn) and amplification at resonance (A) values increase with increasing hardness.

Table 6 shows a normal cushion to have a (Fn) of 52 Hz with cushion from Example 11 being higher at 60 Hz. Cushion from Example 11 will be utilized later as an example of a good performer.

Cushion from Example 15 is an example of cushions yielding a large static deflection. This cushion will be utilized later as an example of a good performer.

It should be noted that Example formulation 15 cushions of the Standard size yields the highest insertion loss for that size. This along with comparative results for the cushions from Example 14 in the Standard Medium & Thin sizes leads one to believe that the thickness as worn preferably should be less than 0.5 inch.

TABLE 6

PHYSICAL PROPERTIES OF SELECTED DYNAMICALLY STIFF MOLDED PV CUSHIONS

|             | CUSHION | THICKNESS | DEFLECTION* | APPARANT | Calc. NRR ON MODEL (dB) | | | TRANSMIS. | |
|-------------|---------|-----------|-------------|----------|-------------------------|---|---|-----------|---|
|             |         |           |             |          | 1000 | 2000 | 3000 | Fn | A |
| Softest     | 19      | 0.405     | 0.0625 (15.4%) | 15.1 | 26.4 | 28.3 | 29.3 | 208 | 3.0 |
|             | 4       | 0.662     | 0.2400 (36.3%) | 13.1 | 24.8 | 27.6 | 28.9 | 132 | 2.8 |
| 2nd Softest | 18      | 0.411     | 0.0509 (12.4%) | 15.0 | 25.3 | 28.3 | 29.5 | 256 | 3.0 |
|             | 14      | 0.491     | 0.0958 (19.5%) | 13.1 | 25.0 | 27.8 | 29.6 | 164 | 2.8 |
|             | 3       | 0.654     | 0.1539 (23.5%) | 12.9 | 25.1 | 27.0 | 27.8 | 132 | 3.1 |
| 3rd Softest | 17      | 0.412     | 0.0340 (8.3%)  | 14.8 | 25.8 | 27.8 | 29.5 | 324 | 4.0 |
|             | 2       | 0.662     | 0.01229 (18.6%) | 12.3 | 25.0 | 27.0 | 27.7 | 160 | 3.0 |
| 4th Softest | 16      | 0.411     | 0.0356 (8.7%)  | 12.9 | 26.2 | 28.5 | 28.7 | 336 | 4.4 |

TABLE 6-continued
PHYSICAL PROPERTIES OF SELECTED DYNAMICALLY STIFF MOLDED PV CUSHIONS

| | CUSHION | THICKNESS | DEFLECTION* | APPARANT | Calc. NRR ON MODEL (dB) 1000 | 2000 | 3000 | TRANSMIS. Fn | A |
|---|---|---|---|---|---|---|---|---|---|
| | 1 | 0.669 | 0.0514 (8.1%) | 12.6 | 24.9 | 27.3 | 27.7 | 300 | 4.3 |
| Hardest | 20 | 0.418 | 0.0166 (4.0%) | 13.4 | 26.4 | 28.3 | 28.8 | 504 | 8.0 |
| | 5 | 0.701 | 0.0487 (6.7%) | 10.8 | 25.1 | 26.2 | 26.2 | 356 | 6.2 |
| No MeCl, No | 15 | 0.514 | 0.1961 (38.2%) | 8.5 | 25.5 | 27.8 | 29.0 | 200 | 3.7 |
| | 13 | 0.651 | 0.2820 (43.3%) | 9.3 | — | — | 29.4 | 156 | 3.1 |
| Close to Normal | 11 | 0.654 | 0.2256 (34.5%) | 8.6 | 22.1 | 25.5 | 27.1 | 60 | 5.7 |
| Normal | Normal | 0.641 | 0.1497* | 5.9 | 20.7 | — | 26.7 | 52 | 15.9 |

*Deflection New = 0.0807; Deflection for a used Cushion = 0.3133.

TABLE 7
AVERAGE DYNAMIC PROPERTIES FOR STANDARD & THIN SIZED DYNAMICALLY STIFF CUSHIONS

| | Av. Thickness (In) | Av. Density (#/ft$^3$) | Av. Fn (Hz) | Av. A (dB) |
|---|---|---|---|---|
| Example 4 Softest | 0.534 | 14.1 | 170 | 2.9 |
| Example 18 2nd Softest | 0.533 | 14.0 | 194 | 3.1 |
| Example 17 3rd Softest | 0.537 | 13.6 | 242 | 3.5 |
| Example 1 4th Softest | 0.540 | 12.8 | 318 | 4.4 |
| Example 2 Hardest | 0.560 | 12.1 | 430 | 7.1 |

TABLE 8
CUSHION SHORE 00 DUROMETER -VS- TEMPERATURE (Instant Readings)

| CUSHION Example | 7° C. | 22° C. | 41° C. |
|---|---|---|---|
| 19 | 67 | 34 | 22 |
| 4 | 68 | 29 | 15 |
| 18 | 77 | 40 | 24 |
| 14 | 70 | 35 | 20 |
| 3 | 73 | 36 | 19 |
| 17 | 77 | 50 | 28 |
| 2 | 72 | 36 | 20 |
| 16 | 80 | 47 | 26 |
| 1 | 81 | 49 | 25 |
| 2 | 90 | 75 | 44 |
| 5 | 87 | 65 | 37 |
| 15 | 74 | 37 | 17 |
| 15 | 75 | 39 | 17 |
| 11 | 41 | 20 | 11 |
| 1* | 81 | 60 | 40 |
| 6 | 75 | 45 | 22 |
| 7 | 78 | 52 | 20 |
| 8 | 73 | 35 | 15 |
| 9 | 71 | 28 | 16 |
| 21 | 49 | 48 | 45 |
| 10 | 34 | 33 | 32 |
| 12 | 65 | 33 | 22 |
| 1** | 80 | 52 | 32 |
| Normal | 61 | 50 | 40 |

*In-mold coated
**Shiny surface

Attenuation Testing—Ansi S3.19

Figure 12:
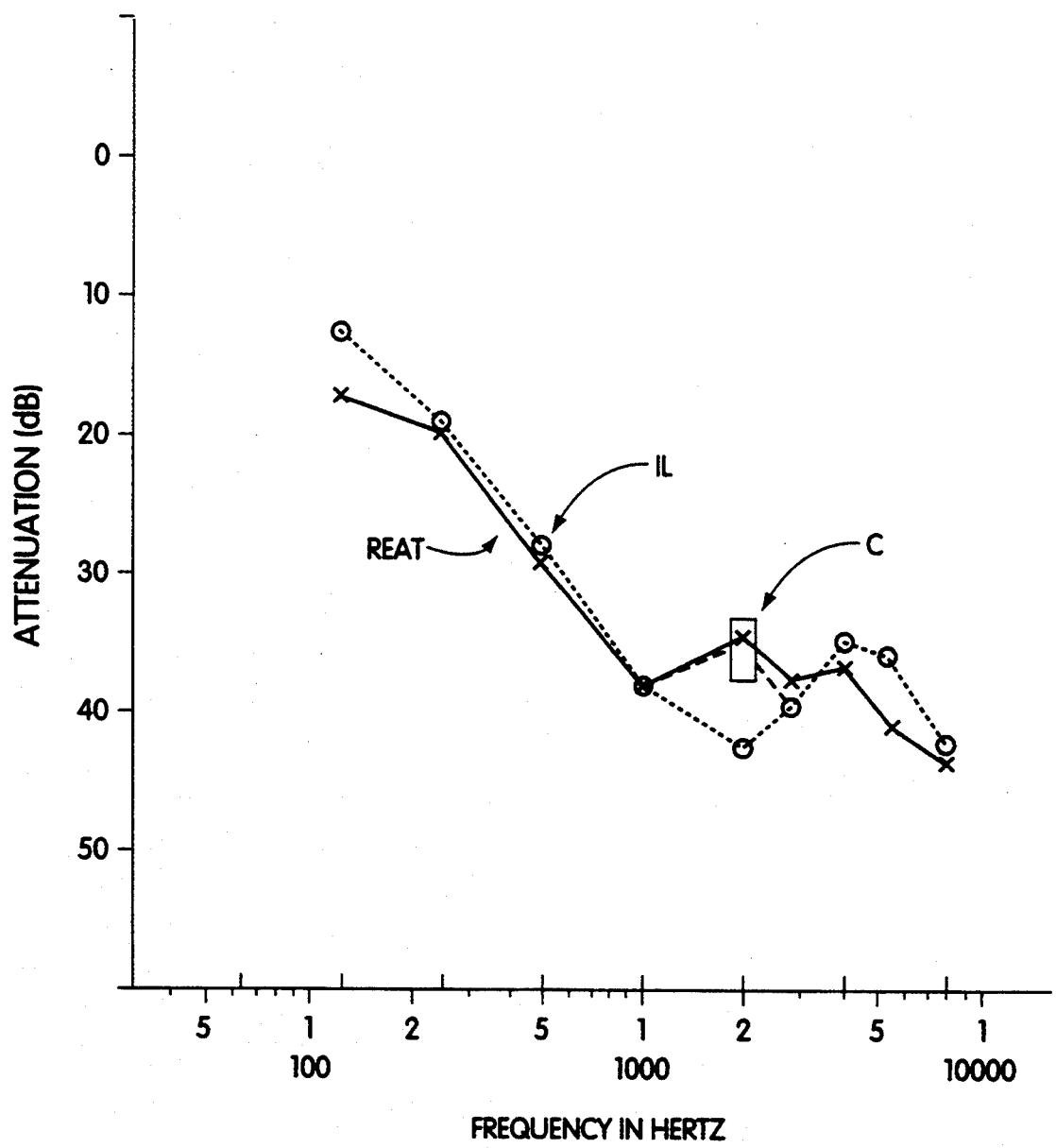
FIG. 12 shows a comparison of REAT and IL values as a function of frequency for an earmuff.

Four earmuff cushions as alluded to earlier were selected for Real-Ear Attenuation Testing at Threshold (REAT) by ANSI S3.19 and comparison made of those attenuation results with insertion loss values. All attenuation results were in conformance with ANSI S3.19 except that five subjects were employed. FIG. 12 shows the comparison of REAT to IL values as a function of frequency for Model 1000 Earmuffs with dynamically stiff cushions, Example 11 (Std.). This figure shows the insertion law (IL) (calculated NRR=22) vs. Real Ear Attenuation at threshold (REAT) (NRR=24) comparison for Model 1000 ear muffs with dynamically stiff cushions of example 11. The bone conduction limited area is shown as B. These cushions were selected to be close to but superior to Normal Model 1000 cushions. Tables 9 A and B show the individual subject data along with appropriate calculations.

TABLE 9A
DIXONS OUTLIER TEST: EXTREME MEANS
Mean attenuation in dB across trials

| Subj. | 125* | 250 | 500 | 1000 | 2000 | 3150 | 4000 | 6300 | 8000 |
|---|---|---|---|---|---|---|---|---|---|
| DVF | 14.3 | 19.3 | 31.0 | 39.3 | 32.3 | 37.7 | 35.0 | 40.3 | 43.7 |
| JEF | 15.0 | 18.3 | 29.7 | 37.7 | 35.3 | 36.3 | 37.3 | 42.3 | 40.3 |
| MG | 16.7 | 18.3 | 26.7 | 36.7 | 34.7 | 37.3 | 36.3 | 40.3 | 44.3 |
| BAK | 21.7 | 23.7 | 27.0 | 37.0 | 36.7 | 37.7 | 38.3 | 42.3 | 43.7 |
| JRM | 14.3 | 17.7 | 28.3 | 36.3 | 31.7 | 36.3 | 37.0 | 38.7 | 39.7 |
| Mean | 16.4 | 19.5 | 28.5 | 37.4 | 34.1 | 37.1 | 36.8 | 40.8 | 42.3 |
| Min. | 14.3 | 17.7 | 26.7 | 36.3 | 31.7 | 36.3 | 35.0 | 39.7 | 38.7 |
| Max. | 21.7 | 23.7 | 31.0 | 39.3 | 36.7 | 37.7 | 38.3 | 42.3 | 44.3 |

*⅓ Octave-Band Frequency

TABLE 9B
INDIVIDUAL SUBJECT DATA

| Test ID: | 150009 | Samples: | 1 |
|---|---|---|---|
| Device: | Model 1000, Cushions | Comfort: | 3.2 |
| Date: | 2/15/93 | Comments: | Tested w/150008, −10, −11 |
| Position: | Over the Head (OTH) | | |

| Subj. | Trial | 125** | 250 | 500 | 1000 | 2000 | 3150 | 4000 | 6300 | 8000 | 125 | Com. | Birt. Breadt | Head Height | NRR* |
|---|---|---|---|---|---|---|---|---|---|---|---|---|---|---|---|
| DVF | 1 | 15 | 20 | 33 | 42 | 34 | 37 | 36 | 40 | 45 | 15 | | 136 | 126 | 25.6 |
| | 2 | 12 | 19 | 31 | 38 | 30 | 37 | 32 | 41 | 43 | 16 | | | | |
| | 3 | 16 | 19 | 29 | 38 | 33 | 39 | 37 | 40 | 43 | 10 | 4 | | | |
| JEF | 1 | 15 | 17 | 26 | 38 | 33 | 39 | 38 | 43 | 37 | 11 | | 133 | 126 | 25.0 |
| | 2 | 14 | 19 | 33 | 41 | 37 | 34 | 38 | 43 | 43 | 13 | | | | |
| | 3 | 16 | 19 | 30 | 34 | 36 | 36 | 36 | 41 | 41 | 18 | 2 | | | |
| MG | 1 | 17 | 19 | 26 | 39 | 32 | 34 | 36 | 43 | 43 | 15 | | 136 | 118 | 23.7 |
| | 2 | 17 | 15 | 28 | 35 | 36 | 39 | 35 | 37 | 43 | 17 | | | | |

TABLE 9B-continued

INDIVIDUAL SUBJECT DATA

|      | 3 | 16   | 21   | 26   | 36   | 36   | 39   | 38   | 41   | 47   | 16   | 3    |       |       |      |
|------|---|------|------|------|------|------|------|------|------|------|------|------|-------|-------|------|
| BAK  | 1 | 24   | 25   | 27   | 36   | 38   | 39   | 38   | 42   | 41   | 19   |      | 150   | 143   | 28.0 |
|      | 2 | 21   | 25   | 28   | 38   | 37   | 38   | 39   | 43   | 45   | 17   |      |       |       |      |
|      | 3 | 20   | 21   | 26   | 37   | 35   | 36   | 38   | 42   | 45   | 18   | 3    |       |       |      |
| JRM  | 1 | 15   | 19   | 31   | 36   | 30   | 37   | 38   | 39   | 39   | 13   |      | 141   | 133   | 24.9 |
|      | 2 | 15   | 17   | 27   | 37   | 32   | 36   | 37   | 39   | 40   | 14   |      |       |       |      |
|      | 3 | 13   | 17   | 27   | 36   | 33   | 36   | 36   | 38   | 40   | 17   | 4    |       |       |      |
| Mean | + | 16.4 | 19.5 | 28.5 | 37.4 | 34.1 | 37.1 | 36.8 | 40.8 | 42.3 | 15.3 | Mean | 139.2 | 129.2 | 25.4 |
| sd(10) |  | 3.1 | 2.7 | 2.5 | 2.1 | 2.5 | 1.8 | 1.7 | 1.9 | 2.7 | 2.6 | sd(5) | 6.7 | 9.4 | 1.6 |
| sd(5)  |  | 3.1 | 2.4 | 1.8 | 1.2 | 2.1 | 0.7 | 1.2 | 1.6 | 2.2 |     |       |     |     |     |
| Q-Value |  | 26.2 | 22.6 | 26.7 | 33.1 | 27.9 |   | 32.4 |   | 38.1 |   |       |     |     |     |

Figure 13:
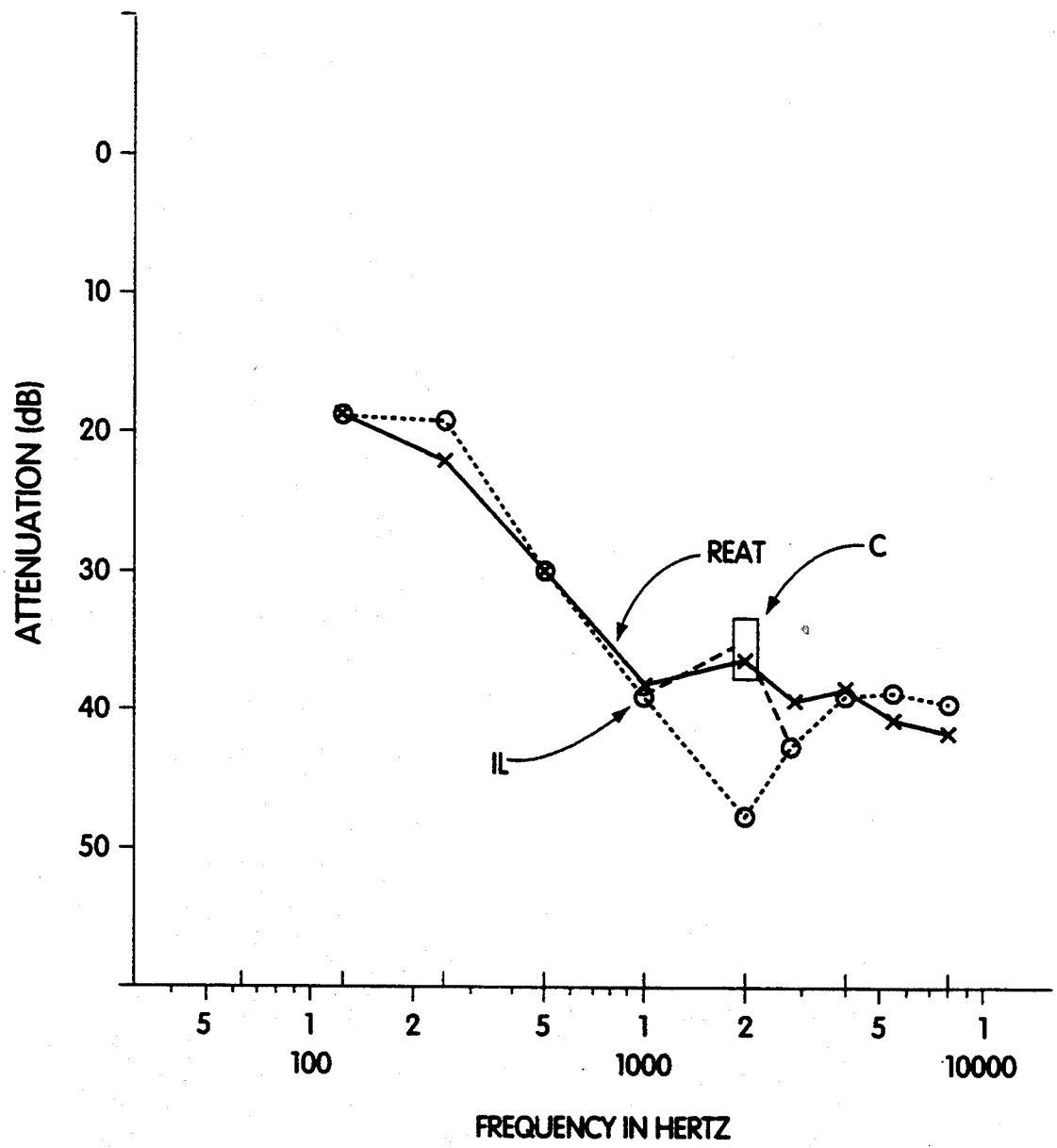
FIG. 13 shows a comparison of REAT to IL values as a function of frequency for earmuffs.

NRR (2sd) = 23.9
NRR (1sd) = 26.5
NRR (0sd) = 29.2
NRR* - Individual 2sd NRR
**⅓ Octave-Band Frequency
Band Force (N)
Before: 11.5
   Dimensions in mm FIG. 13 shows the comparison of REAT (NRR=25) to IL values (calculated NRR=25) as a function of frequency for Model 1000 Earmuffs with dynamically stiff cushions of Example 5 (Std.). C is the bone conduction limited area. These cushions were selected as having close to marginal static deflection for problem subjects. Tables 10 A and B show the individual subject data along with appropriate calculations.

TABLE 10A

DIXONS OUTLIER TEST: EXTREME MEANS
Mean attenuation in dB across trials

TABLE 10A-continued

DIXONS OUTLIER TEST: EXTREME MEANS
Mean attenuation in dB across trials

| Subj. | 125* | 250 | 500  | 1000 | 2000 | 3150 | 4000 | 6300 | 8000 |
|-------|------|-----|------|------|------|------|------|------|------|
| MG    | 20.3 | 22.0 | 29.3 | 36.0 | 35.7 | 36.0 | 33.0 | 33.3 | 36.3 |
| BAK   | 22.7 | 25.7 | 29.7 | 33.3 | 35.7 | 33.7 | 34.0 | 35.3 | 36.3 |
| JRM   | 20.7 | 23.3 | 31.7 | 37.7 | 33.0 | 36.7 | 33.0 | 41.3 | 40.7 |
| Mean  | 18.9 | 22.7 | 29.6 | 35.3 | 34.6 | 33.4 | 32.9 | 35.3 | 37.1 |
| Min.  | 10.7 | 19.0 | 26.0 | 33.3 | 32.7 | 28.0 | 31.7 | 31.3 | 34.3 |
| Max.  | 22.7 | 25.7 | 31.7 | 37.7 | 36.0 | 36.7 | 34.0 | 41.3 | 40.7 |

*⅓ Octave-Band Frequency

TABLE 10B

INDIVIDUAL SUBJECT DATA

Test ID: 150010     Samples: 1
Device: Model 1000, Cushions    Comfort: 3.8
Date: 2/12/93    Comments: Tested w/150008, −09, −11
Position: Over the Head (OTH)

| Subj. | Trial | 125** | 250 | 500 | 1000 | 2000 | 3150 | 4000 | 6300 | 8000 | 125 | Com. | Birt. Breadt | Head Height | NRR* |
|-------|-------|-------|-----|-----|------|------|------|------|------|------|-----|------|--------------|-------------|------|
| DVF   | 1 | 10 | 19 | 26 | 39 | 33 | 28 | 34 | 28 | 35 | 7  |   | 136 | 126 | 19.2 |
|       | 2 | 7  | 19 | 26 | 31 | 33 | 24 | 25 | 39 | 38 | 12 |   |     |     |      |
|       | 3 | 15 | 19 | 26 | 33 | 33 | 32 | 36 | 27 | 30 | 12 | 4 |     |     |      |
| JEF   | 1 | 17 | 20 | 32 | 36 | 36 | 35 | 34 | 37 | 37 | 20 |   | 133 | 125 | 25.4 |
|       | 2 | 20 | 25 | 31 | 37 | 36 | 31 | 35 | 35 | 39 | 18 |   |     |     |      |
|       | 3 | 23 | 25 | 31 | 33 | 36 | 32 | 30 | 34 | 37 | 23 | 4 |     |     |      |
| MG    | 1 | 19 | 22 | 30 | 37 | 37 | 37 | 32 | 35 | 38 | 18 |   | 136 | 118 | 27.7 |
|       | 2 | 21 | 21 | 29 | 36 | 33 | 34 | 33 | 32 | 36 | 18 |   |     |     |      |
|       | 3 | 21 | 23 | 29 | 35 | 37 | 37 | 34 | 33 | 35 | 18 | 3 |     |     |      |
| BAK   | 1 | 24 | 28 | 32 | 30 | 32 | 31 | 31 | 38 | 39 | 23 |   | 150 | 143 | 25.3 |
|       | 2 | 24 | 25 | 29 | 35 | 37 | 33 | 33 | 32 | 34 | 20 |   |     |     |      |
|       | 3 | 20 | 24 | 28 | 35 | 38 | 37 | 36 | 36 | 17 | 3  |   |     |     |      |
| JRM   | 1 | 18 | 23 | 34 | 40 | 35 | 38 | 35 | 41 | 41 | 23 |   | 141 | 133 | 27.5 |
|       | 2 | 23 | 23 | 32 | 36 | 33 | 36 | 32 | 42 | 41 | 20 |   |     |     |      |
|       | 3 | 21 | 24 | 29 | 37 | 31 | 36 | 32 | 41 | 40 | 20 | 5 |     |     |      |
| Mean  | + | 18.9 | 22.7 | 29.6 | 35.3 | 34.6 | 33.4 | 32.9 | 35.3 | 37.1 | 17.9 | Mean | 139.2 | 129.2 | 25.2 |
| sd(10) |  | 4.9 | 2.7 | 2.4 | 2.7 | 2.3 | 3.9 | 3.0 | 4.5 | 2.9 | 4.5 | sd(5) | 6.7 | 9.4 | 3.5 |
| sd(5)  |  | 4.7 | 2.4 | 2.3 | 1.6 | 1.6 | 3.4 | 0.8 | 3.7 | 2.3 |     |       |     |     |     |
| Q-Value |  | 25.1 | 25.9 | 27.9 | 29.9 | 28.9 |   | 25.3 |   | 29.9 |   |       |     |     |     |

NRR (2sd) = 23.6
NRR (1sd) = 26.9
NRR (0sd) = 30.0
NRR* - Individual 2sd NRR
**⅓ Octave-Band Frequency
Band Force (N)
Before: 12.3
After: 12.0
   Dimensions in mm

| Subj. | 125* | 250 | 500 | 1000 | 2000 | 3150 | 4000 | 6300 | 8000 |
|-------|------|-----|-----|------|------|------|------|------|------|
| DVF   | 10.7 | 19.0 | 26.0 | 34.3 | 32.7 | 28.0 | 31.7 | 31.3 | 34.3 |
| JEF   | 20.0 | 23.3 | 31.3 | 36.3 | 36.0 | 32.7 | 33.0 | 35.3 | 37.7 |

Figure 14:
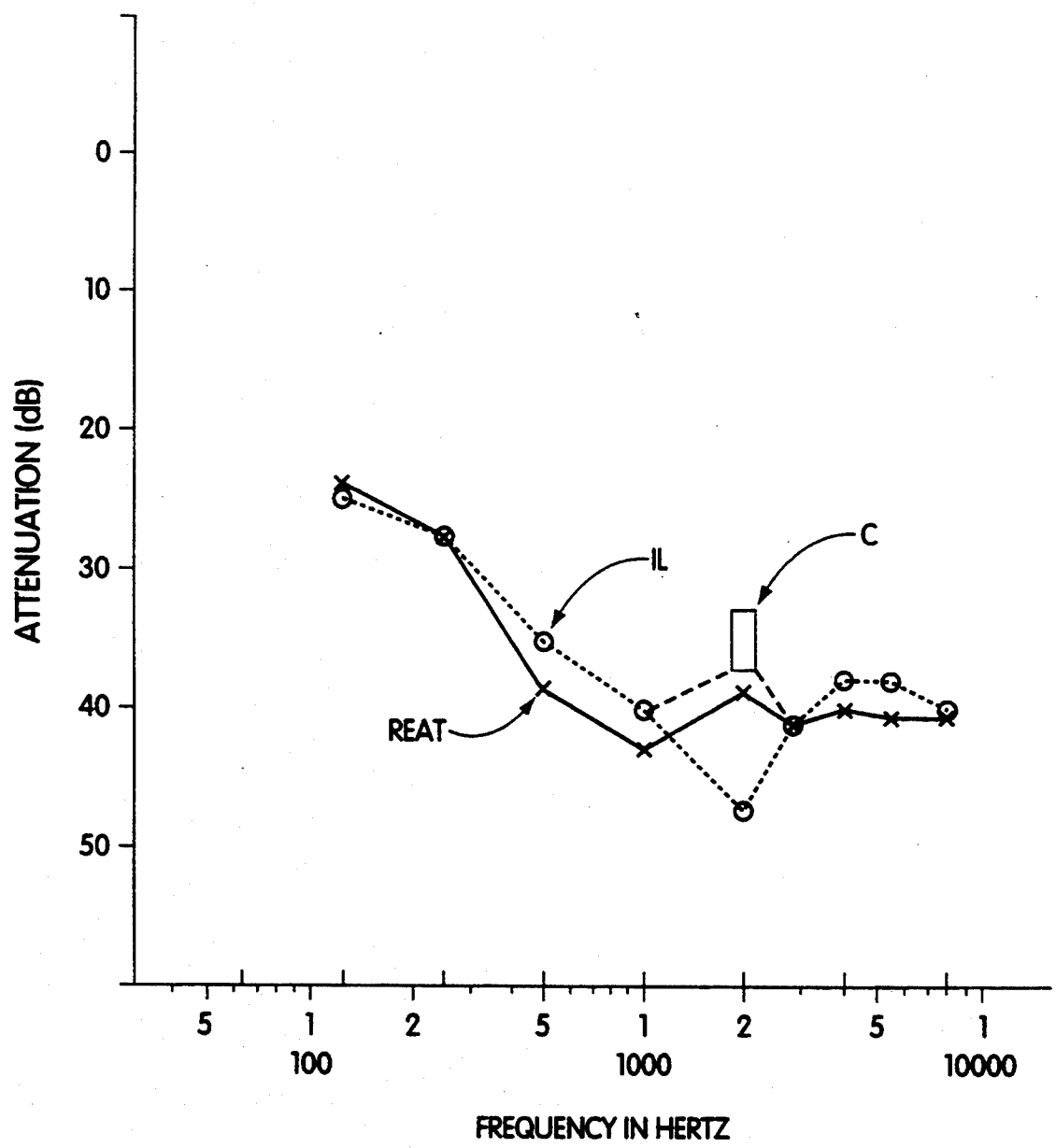
FIG. 14 shows a comparison of REAT to IL values as a function of frequency for earmuffs.

FIG. 14 shows the comparison of REAT (NRR=29) to IL values (calculated NRR=29) as a function of frequency for Model 3000 Earmuffs with dynamically stiff cushions of Example 14 (Med.). The bone conduction limited area is shown as C. These cushions were selected because of their superior IL performance on Model 000 Earmuffs. Tables 11 A and B show the individual subject data along with appropriate calculations.

TABLE 11A

DIXONS OUTLIER TEST: EXTREME MEANS
Mean attenuation in dB across trials

| Subj. | 125* | 250 | 500 | 1000 | 2000 | 3150 | 4000 | 6300 | 8000 |
|-------|------|-----|-----|------|------|------|------|------|------|
| DVF   | 23.0 | 27.7 | 39.3 | 42.0 | 38.7 | 41.0 | 40.7 | 41.0 | 42.3 |
| JEF   | 21.7 | 25.3 | 37.3 | 43.0 | 34.7 | 41.3 | 37.7 | 41.3 | 40.0 |
| MG    | 23.0 | 24.7 | 36.7 | 41.7 | 40.0 | 40.3 | 38.0 | 39.3 | 41.0 |
| BAK   | 27.3 | 31.7 | 38.3 | 44.7 | 44.7 | 43.0 | 43.3 | 41.0 | 39.3 |
| JRM   | 24.0 | 27.0 | 39.7 | 43.7 | 33.7 | 40.0 | 40.3 | 41.0 | 40.0 |
| Mean  | 23.8 | 27.3 | 38.3 | 43.0 | 38.3 | 41.1 | 40.0 | 40.7 | 40.5 |
| Min.  | 21.7 | 24.7 | 36.7 | 41.7 | 33.7 | 40.0 | 37.7 | 39.3 | 39.3 |
| Max.  | 27.3 | 31.7 | 39.7 | 44.7 | 44.7 | 43.0 | 43.3 | 41.3 | 42.3 |

*⅓ Octave-Band Frequency

Figure 16:
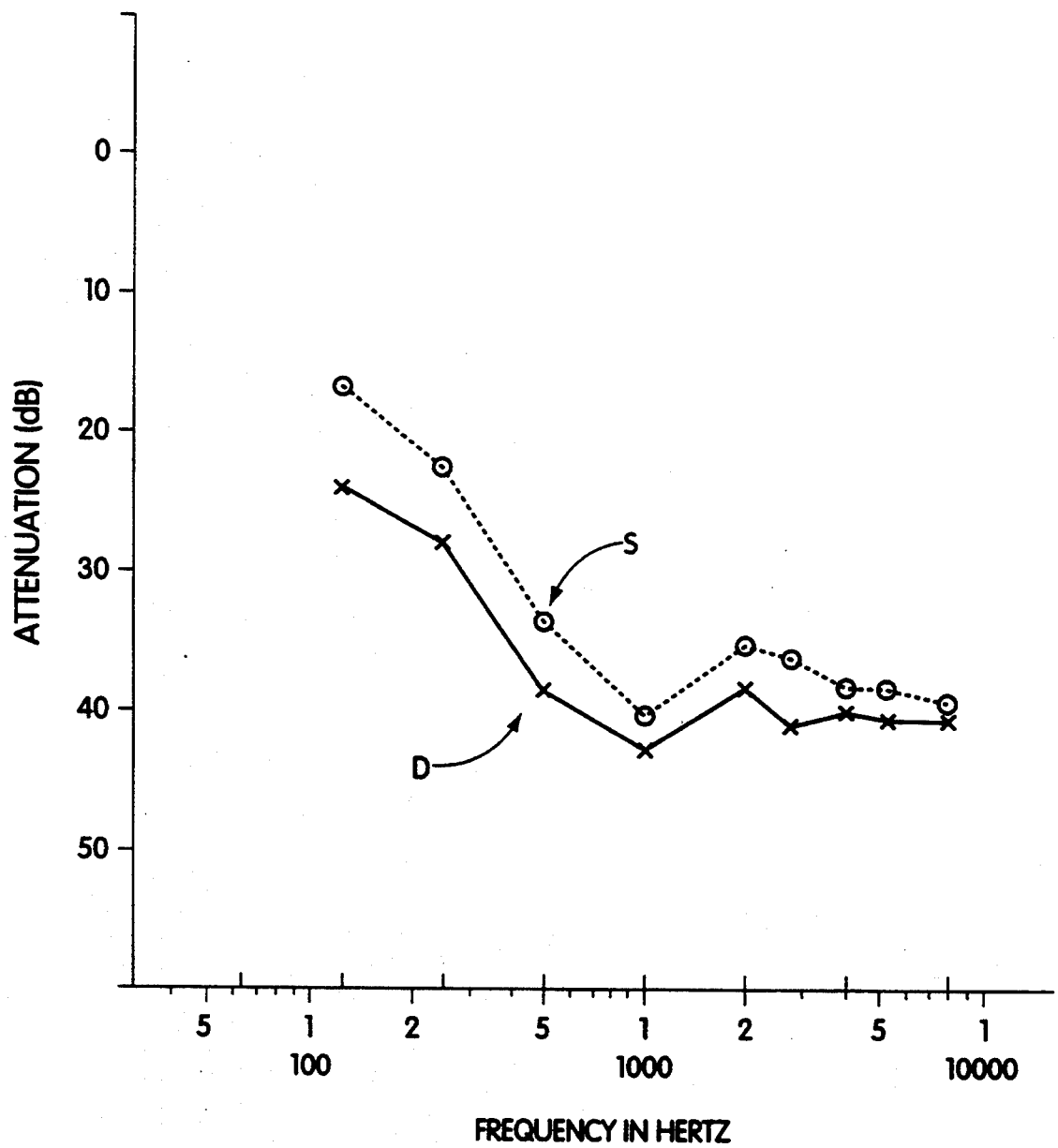
FIG. 16 shows REAT comparisons.

FIG. 16 shows a REAT comparison for Model 3000 Earmuffs having dynamically stiff cushions (D) (NRR=29) of Example 14 (Med.)as compared to the same earmuffs having their normal cushions (S) (NRR=25).

All of these results from FIG. 11 through FIG. 16 shows the close correlation between REAT and IL and the superior performance of dynamically stiff cushions over normal cushions.

Coatings

Finally, sample cushions were coated with an in-mold aliphatic sky blue polyurethane, Aliphlex MPM-E180A. The coating was applied in-mold (spraying the mold, 10% solids composition, approximately one mil thick) prior to foam formulation addition (can also be applied alternately to the foam cushion after production). Both coatings were reasonable with the in-mold coating having superior looks and feel. The cushions spray-coated after production resulted in some absorp-

TABLE 11B

INDIVIDUAL SUBJECT DATA

Test ID: 150008  Samples: 1
Device: Model 3000, Cushions  Comfort: 3.8
Date: 2/12/93  Comments: Tested w/ 150009, −10, −11
Position: Over the Head (OTH)

| Subj. | Trial | 125** | 250 | 500 | 1000 | 2000 | 3150 | 4000 | 6300 | 8000 | 125 | Com. | Birt. Breadt | Head Height | NRR* |
|-------|-------|-------|-----|-----|------|------|------|------|------|------|-----|------|--------------|-------------|------|
| DVF   | 1     | 21    | 26  | 39  | 40   | 36   | 41   | 41   | 41   | 43   | 21  |      | 136          | 126         | 30.4 |
|       | 2     | 26    | 31  | 42  | 45   | 40   | 45   | 44   | 40   | 42   | 24  |      |              |             |      |
|       | 3     | 22    | 26  | 37  | 41   | 40   | 37   | 37   | 42   | 42   | 25  | 5    |              |             |      |
| JEF   | 1     | 22    | 23  | 39  | 42   | 34   | 41   | 38   | 42   | 40   | 22  |      | 133          | 126         | 29.8 |
|       | 2     | 21    | 27  | 34  | 46   | 37   | 41   | 38   | 38   | 39   | 23  |      |              |             |      |
|       | 3     | 22    | 26  | 39  | 41   | 33   | 42   | 37   | 44   | 41   | 24  | 3    |              |             |      |
| MG    | 1     | 24    | 24  | 35  | 44   | 39   | 39   | 37   | 40   | 41   | 20  |      | 136          | 118         | 31.7 |
|       | 2     | 22    | 25  | 35  | 41   | 39   | 40   | 37   | 39   | 40   | 23  |      |              |             |      |
|       | 3     | 23    | 25  | 40  | 40   | 42   | 42   | 40   | 39   | 42   | 28  | 3    |              |             |      |
| BAK   | 1     | 28    | 34  | 39  | 44   | 46   | 45   | 44   | 41   | 38   | 26  |      | 150          | 143         | 36.1 |
|       | 2     | 27    | 30  | 38  | 44   | 44   | 42   | 42   | 41   | 38   | 22  |      |              |             |      |
|       | 3     | 27    | 31  | 38  | 46   | 44   | 42   | 44   | 41   | 42   | 26  | 3    |              |             |      |
| JRM   | 1     | 23    | 28  | 40  | 45   | 33   | 40   | 41   | 42   | 40   | 26  |      | 141          | 133         | 31.6 |
|       | 2     | 27    | 26  | 41  | 42   | 35   | 40   | 39   | 40   | 40   | 23  |      |              |             |      |
|       | 3     | 22    | 27  | 38  | 44   | 33   | 40   | 41   | 41   | 40   | 24  | 5    |              |             |      |
| Mean  |       | 23.8  | 27.3 | 38.3 | 43.0 | 38.3 | 41.1 | 40.0 | 40.7 | 40.5 | 23.8 | Mean | 139.2       | 129.2       | 31.9 |
| sd(10)|       | 2.5   | 3.0 | 2.3 | 2.1  | 4.4  | 2.1  | 2.7  | 1.5  | 1.5  | 2.1 | sd(5)| 6.7          | 9.4         | 2.5  |
| sd(5) |       | 2.1   | 2.7 | 1.3 | 1.2  | 4.4  | 1.2  | 2.3  | 0.8  | 1.2  |     |      |              |             |      |
| Q-Value|      | 34.9  | 29.8 | 37.0 | 38.8 | 28.4 |      | 34.8 |      | 38.7 |     |      |              |             |      |

Figure 15:
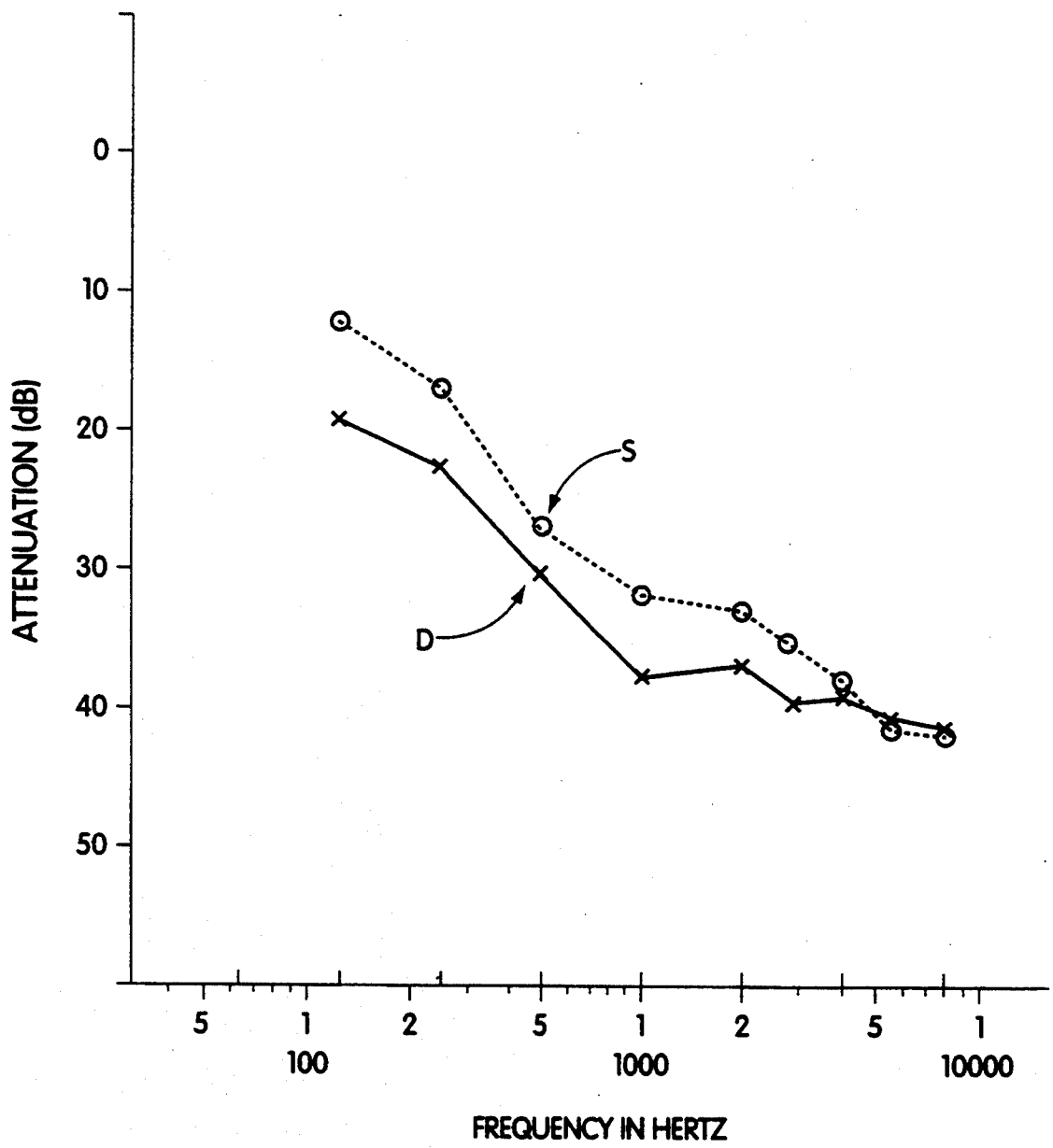
FIG. 15 shows REAT comparisons.

NRR (2sd) = 29.4
NRR (1sd) = 32.6
NRR (0sd) = 35.6
NRR* - Individual 2sd NRR
**⅓ Octave-Band Frequency
Band Force (N)
Before: 13.2
After: 13.5
+ Dimensions in mm FIG. 15 shows a REAT comparison for Model 1000 Earmuffs having dynamically stiff cushions (D) of Example 15 (Med.)(NRR=25) as compared to the same earmuffs having their normal cushions·(S) (NRR=20).

tion into the surface. Table 12 shows insertion loss test results indication that coated cushions yield the same improved low frequency attenuation and estimated NRRs as the uncoated dynamically stiff cushions.

TABLE 12

EFFECT OF TEN COATINGS ON THE IL OF MODEL 1000 EARMUFFS HAVING DYNAMICALLY STIFF CUSHIONS (6415-84A3 STANDARD)

| CUSHION | INSERTION LOSS (dB) | | | | | | | | | NNR | Q FREQ |
|---------|-----|-----|-----|------|------|------|------|------|------|-----|--------|
|         | 125 | 250 | 500 | 1000 | 2000 | 3150 | 4000 | 6200 | 8000 |     |        |
| NORMAL  | 4.0 | 17.7 | 25.8 | 35.1 | 42.4 | 38.4 | 37.5 | 39.2 | 42.9 | 20.7 | 250 |
| IN-MOLD COATED | 19.8 | 21.7 | 31.3 | 33.8 | 44.8 | 35.0 | 33.6 | 37.3 | 40.0 | 24.9 | 250 |
| OUT-OF-MOLD COATED | 21.8 | 21.6 | 31.7 | 34.2 | 44.7 | 36.8 | 34.4 | 37.8 | 40.9 | 25.4 | 250 |

TABLE 12-continued

EFFECT OF TEN COATINGS ON THE IL OF MODEL 1000 EARMUFFS HAVING DYNAMICALLY STIFF CUSHIONS (6415-84A3 STANDARD)

| CUSHION | INSERTION LOSS (dB) | | | | | | | | | NNR | Q FREQ |
|---|---|---|---|---|---|---|---|---|---|---|---|
| | 125 | 250 | 500 | 1000 | 2000 | 3150 | 4000 | 6200 | 8000 | | |
| NOT-COATED | 19.8 | 21.5 | 30.8 | 34.3 | 45.8 | 37.2 | 34.3 | 35.3 | 39.8 | 25.0 | 250 |

In addition to increased attenuation, the cushions of the present invention provide improved ease of manufacture. Many earmuff cushions have been made and tested most of which gave superior low frequency insertion loss and estimated NRRs. REAT and IL values as well as NRRs calculated from them checked each other very well although if questions should arise REAT ANSI S3.19 values could be utilized as a referee. All foam cushions produced of molded polyurethane on foam machinery have an ease of manufacturing advantage (which would also show itself as a low cost manufacturing advantage). Cushions having static defections of about 0.05 inch or greater are preferred for problem subjects with a static deflection of about 0.10 or more being more preferred. Cushions having an Fn as tested in this report of about 52 Hz or more show equal to or superior performance to normal cushions. Cushion which deflect to a thickness of about 0.5 inch or less when compressed (as measured by the static deflection test) are preferred. Cushions with increased contact with the head are preferred. An example of this is the reversed taper shape referred to in FIG. 11 and Table 4 although other thicknesses are certainly applicable.

Applied coatings especially in-mold coatings may be advantageous. Placing molded dynamically stiff cushions into current art bladders may also yield increased performance but at higher cost. The total effect of amplification at resonance (A), is not totally understood at this time. It is felt that cushions having Fn about 52 Hz or less may be useable as low cost cushions of similar performance to the prior-art. However, more highly resilient cushions having Fn of about 52 Hz or less with A of 9.5 dB or more may yield inferior attenuation.

From the above, it can be seen that the improved cushion of the present invention results in at least a 3 to 4 dB increase in attenuation over that obtainable with a conventional muff. In addition, the cushion of the present invention is easier to manufacture than conventional muffs. For example, in addition of the elimination of a bladder, it can be formed directly onto a cushion seal end plate, if desired.

We claim:

1. An acoustical earmuff device comprising a pair of earmuffs fastened to opposite ends of a generally U-shaped connecting band, the earmuff comprising a rigid cup section connected to the band on one side of the cup, and a compliant foam section on the other side of the cup for contact with the wearer, wherein the improvement comprises, using as the foam section a foam material having a low static stiffness, and a high dynamic stiffness, resulting in an earmuff with higher attenuation;
   wherein said foam material has a dynamic spring constant of at least 300 pounds/inch and a dynamic material loss factor of at least 0.25.

2. The earmuff device of claim 1, wherein the foam section has a dynamic spring constant of at least 1,000 pounds/inch.

3. The earmuff device of claim 1, wherein the foam section has a static spring constant of up to 60 pounds/inch.

4. The earmuff device of claim 1, wherein the foam section has a static spring constant of up to 30 pounds/inch.

5. The earmuff device of claim 1, wherein the foam section is a single molded piece.

6. The earmuff device of claim 1, wherein the foam is a polyurethane.

7. The earmuff device of claim 6, wherein the polyurethane is the reaction product of a diisocyanate and a polyol having an isocyanate index of less than about 0.9.

8. The earmuff device of claim 7, wherein at least a portion of the polyol has a functionality of at least 3.

9. The earmuff device of claim 1, wherein the foam additionally contains a polyurethane coating.

10. The earmuff device of claim 1, wherein the cup is attached to the headband through a grommet made of rubber or other elastomeric material.

11. A one piece molded foam earmuff cushion for noise exclusion having a low static stiffness, and a high dynamic stiffness, resulting in higher attenuation when used in an earmuff;
    wherein said foam earmuff cushion has a dynamic spring constant of at least 300 pounds/inch and a dynamic material loss factor of at least 0.25.

12. The earmuff cushion of claim 11, wherein the foam has a dynamic spring constant of at least 1,000 pounds/inch.

13. The earmuff cushion of claim 11, wherein the foam has a static spring constant of up to 60 pounds/inch.

14. The earmuff cushion of claim 11, wherein the foam has a static spring constant of up to 30 pounds/inch.

15. The earmuff cushion of claim 11, wherein the foam is a polyurethane.

16. The earmuff cushion of claim 15, wherein the polyurethane is the reaction product of a diisocyanate and a polyol having an isocyanate index of less than about 0.9.

17. The earmuff cushion of claim 16, wherein at least a portion of the polyol has a functionality of at least 3.

* * * * *